US006942467B2

(12) United States Patent
Deninger et al.

(10) Patent No.: US 6,942,467 B2
(45) Date of Patent: Sep. 13, 2005

(54) UHV COMPATIBLE LEAD THROUGH, DEVICE AND PROCEDURE FOR HIGHLY EFFECTIVE PRODUCTION OF NUCLEAR SPIN POLARIZED $^3$HE AT HIGH POLARIZATION

(76) Inventors: Anselm Deninger, Elsa Brändström Str. 6, Mainz (DE), 55124; Michael Ebert, Bietigheimerstr. 30, Ingersheim (DE), 74379; Jan Hasse, An Der Plantage 95, Mainz (DE), 55120; Werner Heil, Am Gutleuthaus 2, Oppenheim (DE), 55276; Ernst W. Otten, Carl-Orff-Strasse 47, Mainz (DE), 55127; Jörg Schmiedeskamp, Querfeldstrasse 3, Wiesbaden (DE), 65195; Reinhard Surkau, Ribfeldstr. 17, Fürstenfeldbruck (DE), 82258

( * ) Notice: Subject to any disclaimer, the term of this patent is extended or adjusted under 35 U.S.C. 154(b) by 890 days.

(21) Appl. No.: 09/758,006

(22) Filed: Jan. 10, 2001

(65) Prior Publication Data

US 2002/0051712 A1 May 2, 2002

(30) Foreign Application Priority Data

Jan. 11, 2000 (DE) .......................................... 100 00 675

(51) Int. Cl.[7] .............................. F04B 17/04; F01B 7/02; F15B 21/04
(52) U.S. Cl. ........................ 417/313; 417/401; 137/312; 91/52; 91/86; 91/111
(58) Field of Search ................................. 417/313, 401; 137/312; 92/86, 80, 111, 52; 91/169

(56) References Cited

U.S. PATENT DOCUMENTS

| 5,545,396 A | 8/1996 | Albert et al. ................... 424/93 |
|---|---|---|
| 5,557,199 A | 9/1996 | Bowman et al. ............. 324/301 |
| 5,612,103 A | 3/1997 | Driehuys et al. ........... 428/34.7 |
| 5,617,860 A | 4/1997 | Chupp et al. ............. 128/653.4 |
| 5,642,625 A | 7/1997 | Cates, Jr. et al. ............ 62/55.5 |
| 5,785,953 A | 7/1998 | Albert et al. .................. 424/93 |
| 5,789,921 A | 8/1998 | Albert et al. ................ 324/300 |
| 5,809,801 A | 9/1998 | Cates, Jr. et al. ............. 62/637 |
| 5,810,045 A * | 9/1998 | Evans ......................... 137/312 |
| 5,860,295 A | 1/1999 | Cates, Jr. et al. ............. 62/637 |
| 5,941,505 A * | 8/1999 | Nagel ....................... 251/335.2 |
| 6,389,955 B1 * | 5/2002 | Schaefer ......................... 92/86 |

FOREIGN PATENT DOCUMENTS

| DE | 19927773.7 | 8/1968 |
|---|---|---|
| WO | WO95/27438 | 10/1995 |
| WO | WO96/39912 | 12/1996 |
| WO | WO96/40585 | 12/1996 |
| WO | WO97/37239 | 10/1997 |

OTHER PUBLICATIONS

"Determination of the Neutron Electric Form Factor from the Reaction $^3$He (e,én) at Medium Momentum Transfer" The European Physical Journal A 6, pp. 329–344, 1999.

(Continued)

Primary Examiner—Charles G. Freay
(74) Attorney, Agent, or Firm—Ohlandt, Greeley, Ruggiero & Perle, L.L.P.

(57) ABSTRACT

There is provided an ultra high vacuum (UHV) compatible lead-through comprises (a) a housing, (b) a first space, within the housing, connected via a first port to a space outside the UHV-compatible lead through, (c) a second space, within the housing, connected via a second port to a closed system containing a polarized gas, (d) a movable component, separating the first space from the second space via an intermediate space, and (e) seals for limiting a penetration of volatile media from the first space into the second space. The lead through is particularly suited for use in the production of polarized gases, such as $^3$He.

41 Claims, 17 Drawing Sheets

OTHER PUBLICATIONS

"Measurement of the Neutron Electric Form Factor $G_{en}$ at 0.67 (GeV/c) 2 via $^3$He (e, e n)", Physical Review Letters, vol. 83, No. 21, pp. 4257–4260, Nov. 22, 1999.

"$^3$He Neutron Spin–Filter", W. Heil et al., Physica B, pp. 328–335, 1999.

"Nuclear Magnetic Resonance Imaging of Airways in Humans with Use of Hyperpolarized $^3$He", Bachert et al., Magnetic Resonance in Medicine, pp. 192–196, 1996.

"Nuclear Magnetic Resonance Imaging with Hyperpolarised Helium–3", Ebert et al., The Lancet, vol. 347, No. 9011, pp. 1297–1299, May 11, 1996.

"MRI using Hyperpolarized Noble Gases", Kauczor et al, European Radiology 8, pp. 820–827, 1998.

"MR Imaging and Spectroscopy of the Human Chest Using Polarized $^{129}$Xe Gas", Mugler et al., Draft document, Department of Radiology and Biomedical Engineering (University of Virginia Health Sciences Center) & Department of Physics (Princeton University), pp. 1–17, Oct. 2, 1996.

"Ultrafast MR–Imaging of Lung Ventilation Using Hyperolarized Helium–3", Schreiber et al.

"Quantification of Regional Intrapulmonary Oxygen Partial Pressure Evolution During Apnea by $^3$He MRI", Deninger et al., Journal of Magnetic Resonance 141, pp. 207–216, 1999.

"Nuclear Spin–Lattice Relaxation in the prescence of Magnetic–Field Gradients", Schearer et al., Physical Review, vol. 139, No. 5A, pp. 1398–1403, Aug. 30, 1965.

"Relaxation of Spins Due to Field Inhomogeneities in Gaseou Samples at Low Magnetic Fields and Low Pressure", Cates et al., Physical Review A, vol. 37, No. 8, pp. 2877–2855, 1988.

"Polarization of $^3$He Gas by Optical Pumping", Colegrove et al., Physical Review, vol. 132, No. 6, pp. 2561–2573, 1963.

"Optical Pumping in $^3$He with a Laser", Nacher et al., Journal De Physique 46, No. 12, pp. 2057–2073, 1985.

"A Dense Polarized $^3$He Target Based on Compression of Optically Pumped Gas ", Eckert et al., Nuclear Instruments & Methods in physics Research, Section A, pp. 53–65, 1992.

"Accurate Optical Measurement of Nuclear Polarization in Optically Pumped $^3$He Gas", Bigelow et al., Journal de Physique 2, pp. 2159–2179, 1992.

"NMR Calibration of Optical Measurement of Nuclear Polarization in $^3$He", Lorenzon et al., Physical Review A, vol. 47, No. 1, pp. 468–479, 1993.

"Very Long Nuclear Relaxation Times of Spins Polarized Helium 3 in Metal Coated Cells", Heil et al., Physics Letters A, pp. 337–343, 1995.

"$^3$He Neutron Spin–Filter", Heil et al., Physica B, pp. 328–335, 1999.

"Nuclear Relaxation of $^3$He in the Presence of $O_2$" Saam et al., Physical Review A, vol. 52, No. 1, pp. 862–865, 1995.

"Gaseous $^3$He–$^3$He Magnetic Dipolar Spin Relaxation", Newbury et al., Physical Review A, vol. 48, No. 6, pp. 4411–4420, 1993.

"Study of Mechanical Compression of Spin–Polarized $^3$He Gas", Becker et al., Nuclear Instruments and Methods in Physics Research A, pp. 45–51, 1994.

"Spatially Resolved Measurements of Hyperpolarized Gas Properties in the Lung in vino. Part I: Diffusion Coefficient", Chen et al., Center for In Vino Microscopy, Duke University Medical Center, pp. 1–8, Jun. 24, 1999.

"Entwicklung und Test eines $^3$He–Neutron–Spinfilters", Reinhard Surkau, Dissertation, Aug. 1995.

"High–Volume Production of Laser–Polarized $^{129}$Xe", Driehuys et al., Department of Physics, Princeton University, Jul. 8 1996.

"RMP Colloquia : Spin–Exchange Optical Pumping of Noble–Gas Nuclei", Walker et al., Reviews of Modern Physics, vol. 69, No. 2, pp. 629–641, Apr. 1997.

"Polarized Helium–3 Production and Transport System", Hasson et al., Abstract: Magnetic Imaging Technologies, Inc.

"Realization of a Broad Band Neutron Spin Filter with Compressed, Polarized $^3$He Gas", Surkau et al., Nuclear Instruments and Methods in Ohysics Research A, pp. 444–450, 1997.

"Highly Polarized $^3$He for Lung–MRI", Surkau et al., Abstract: Department of Physics, University of D–55099 Mainz, Germany.

* cited by examiner

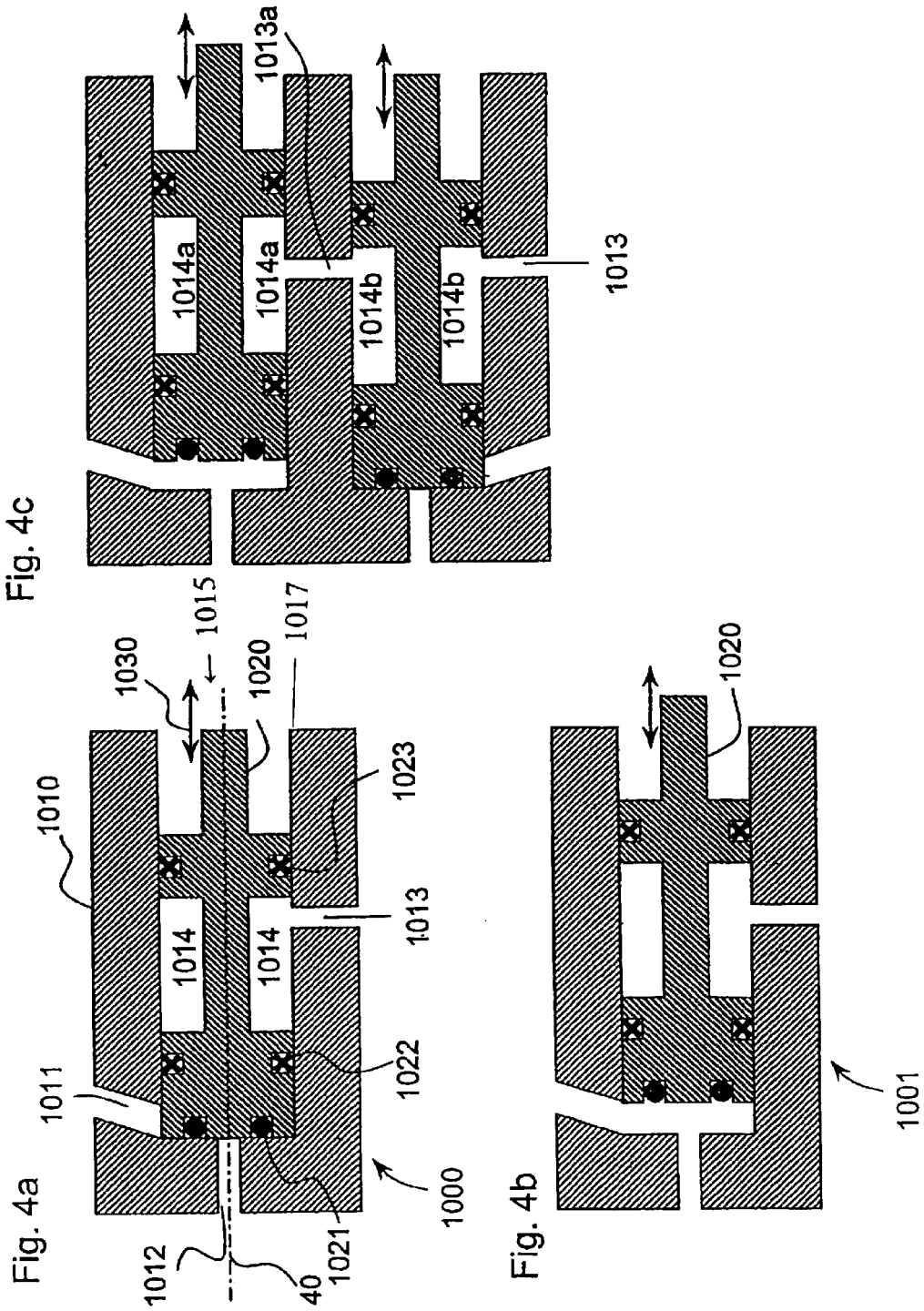

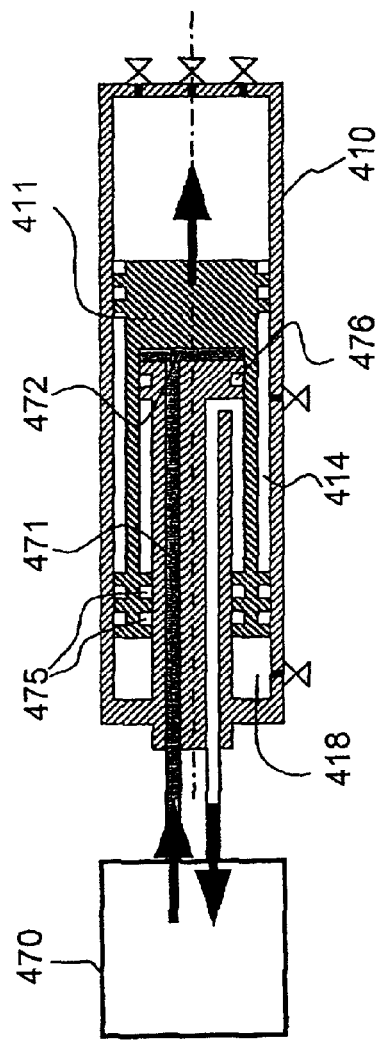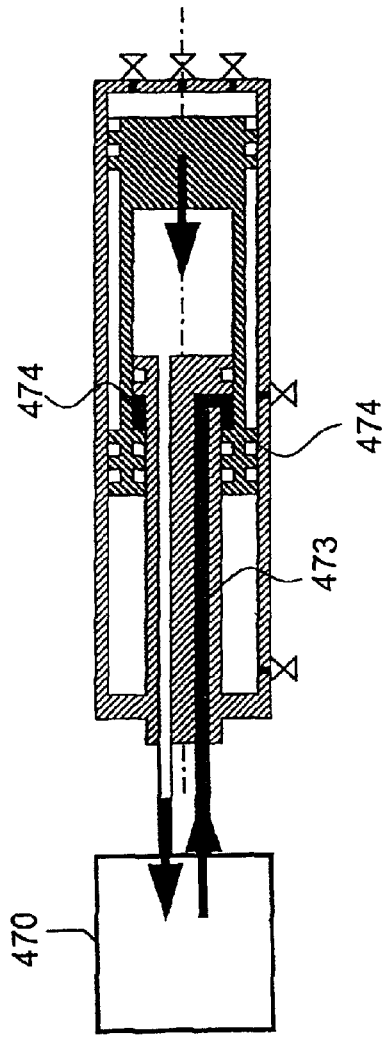
Fig. 6a
Fig. 6b

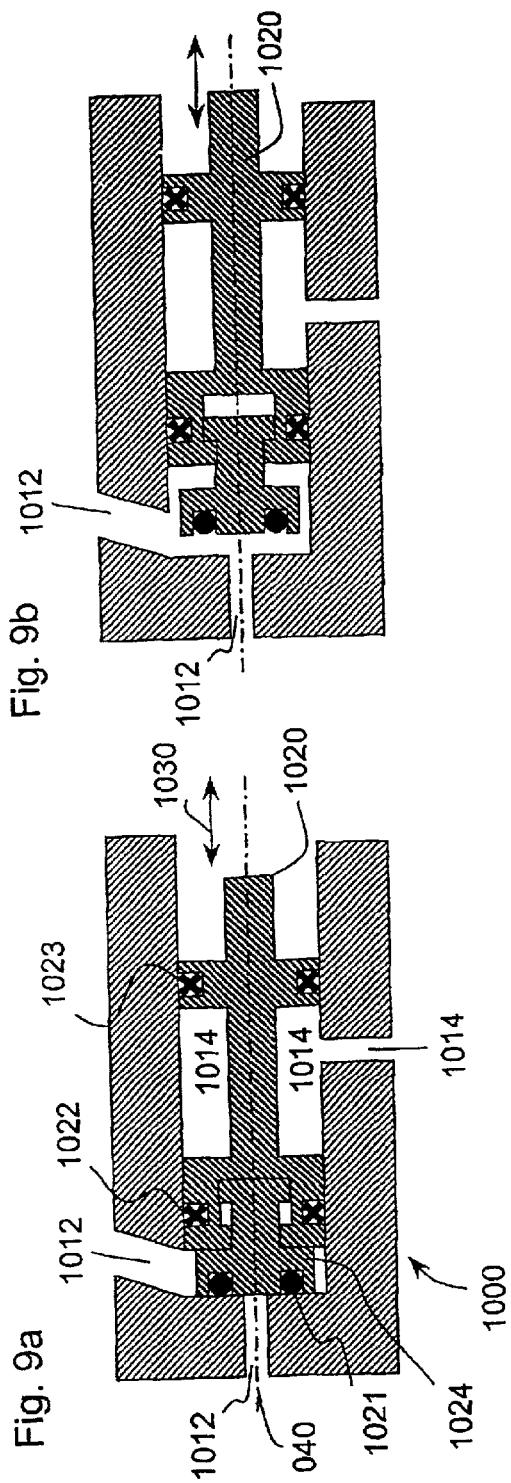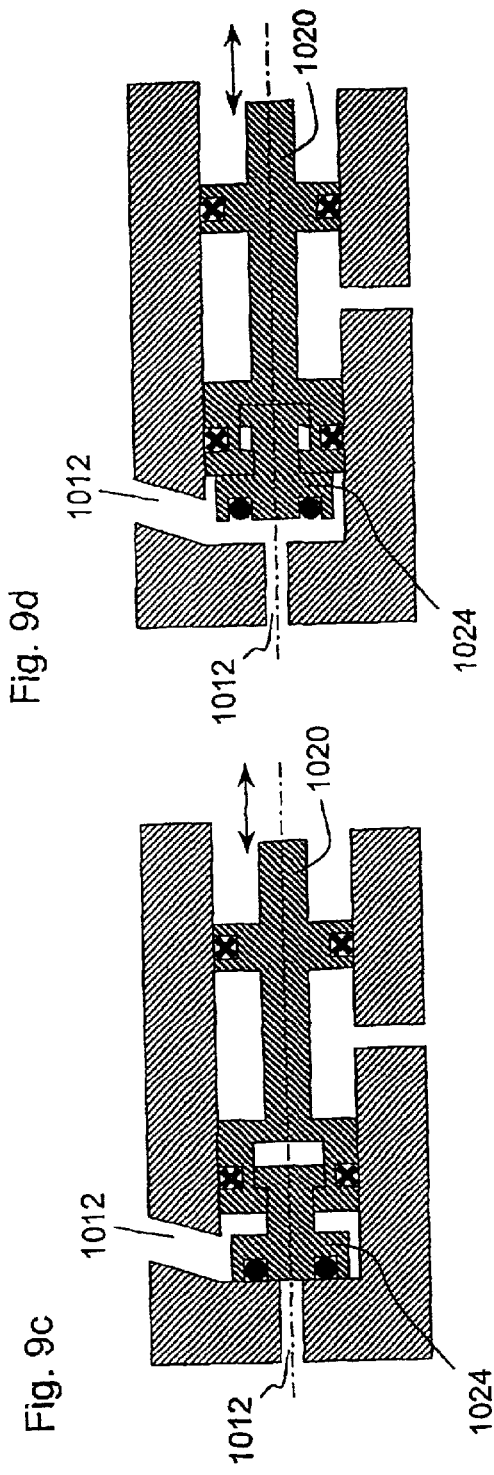

UHV COMPATIBLE LEAD THROUGH, DEVICE AND PROCEDURE FOR HIGHLY EFFECTIVE PRODUCTION OF NUCLEAR SPIN POLARIZED ³HE AT HIGH POLARIZATION

FIELD OF THE INVENTION

The invention comprises an UHV-compatible lead through, a device and a procedure for the production of polarized gases, in particular nuclear spin polarized ³Helium gas, called "Helium-3-Polarizer". They are characterized by achieving simultaneously high production rates for polarized atoms and a high degree of final polarization.

DISCUSSION OF THE BACKGROUND ART

Nuclear spin polarized ³He gas is being applied for a variety of research experiments in physics as documented for instance by the following publications:

J. Becker, H. G. Andresen, J. R. M. Annand, K. Aulenbacher, K. Beuchel, J. Blume-Werry, Th. Dombo, P. Drescher, M. Ebert, D. Eyl, A. Frey, P. Grabmayr, T. Großmann, P. Hartmann, T. Hehl, W. Heil, C. Herberg, J. Hoffmann, J. D. Kellie, F. Klein, K. Livingston, M. Leduc, M. Meyerhoff, H. Möller, Ch. Nachtigall, A. Natter, M. Ostrick, E. W. Otten, R. O. Owens, S. Plützer, E. Reichert, D. Rohe, M. Schäfer, H. Schmieden, R. Sprengard, M. Steigerwald, K.-H. Steffens, R. Surkau, Th. Walcher, R. Watson and E. Wilms; "Determination of the Neutron Electric Form Factor from the Reaction 3He(e; e'n') at Medium Momentum Transfer"; Eur. Phys. J. A 6, (1999) 329–344

D. Rohe, P. Bartsch, D. Baumann, J. Becker, J. Bermuth, K. Bohinc, R. Böhm, S. Buttazzoni, T. Caprano, N. Clawiter, A. Deninger, S. Derber, M. Ding, M. Distler, A. Ebbes, M. Ebert, I. Ewald, J. Friedrich, J. M. Friedrich, R. Geiges, T. Großmann, M. Hauger, W. Heil, A. Honegger, P. Jennewein, J. Jourdan, M. Kabrau, A. Klein, M. Kohl, K. W. Krygier, G. Kubon, A. Liesenfeld, H. Merkel, K. Merle, P. Merle, M. Mühlbauer, U. Müller, R. Neuhausen, E. W. Otten, Th. Petitjean, Th. Pospischil, M. Potokar, G. Rosner, H. Schmieden, I. Sick, S. Širca, R. Surkau, A. Wagner, Th. Walcher, G. Warren, M. Weis, H. Woehrle, M. Zeier; "Measurement of the neutron electric form factor Gen at 0.67 (GeV/c)2 via ", Phys. Rev. Lett. 83 (1999) 4257

W. Heil, J. Dreyer, D. Hofmann, H. Humblot, E.-Levievre-Berna, F. Tasset; "³He neutron spin-filter"; Physica B 267–268 (1999) 328–335).

In magnetic resonance tomography (MRT) for medical applications also spin polarized nuclei other than the usual protons, namely, helium-3 (³He) and xenon-129 ($^{129}$Xe), are being discussed nowadays. These spin polarized gases are suited in particular for investigating the ventilation of the lung. This is being described for instance in the following publications:

P. Bachert, L. R. Schad, M. Bock, M. V. Knopp, M. Ebert, T. Großmann, W. Heil, D. Hofmann, R. Surkau, E. W. Otten; "Nuclear Magnetic Resonance Imaging of Airways in Humans with Use of Hyperpolarized ³He "; MRM 36 (1996) 192–196;

M. Ebert, T. Großmann, W. Heil, E. W. Otten, R. Surkau, M. Leduc, P. Bachert, M. V. Knopp, L. R. Schad, M. Thelen; "Nuclear magnetic resonance imaging with hyperpolarized ³He"; THE LANCET, 347 (1996) 1297–1299;

H.-U. Kauczor, R. Surkau, T. Roberts; "MRI using hyperpolarized noble gases"; Eur. Radiol. (8) (1998) 820–827, J. P. Mugler, B. Driehuys, J. R. Brookeman, G. D. Cates, S. S. Berr, R. G. Bryant, T. M. Daniel, E. E. de Lange, J. H. Downs Jr, C. J. Erickson, W. Happer, D. P. Hinton, N. F. Kassel, T. Maier, C. D. Phillips, B. T. Saam, K. L. Sauer, M. E. Wagshul; "MR Imaging and Spectroscopy Using Hyperpolarized $^{129}$Xe Gas: Preliminary Human Results"; MRM 37 (1997) 809–815.

as well as in the patent applications:

WO9527438A1 of 4.4.1995, "Magnetic Resonance Imaging using hyperpolarized Noble Gases" and WO9737239A1 of 28.2.97, "Enhancement of NMR and MRI in the presence of hyperpolarized Noble Gases".

The term "Polarization degree" (P) indicates that fraction of atoms, the nuclear spins (I) of which are oriented together with their magnetic moments ($\mu_I$) along the direction of an external magnetic field (B). In order to enable MRT on a gaseous species, one requires B to be 4 to 5 orders of magnitude higher than $P_{Boltzmann}$ which is the degree of polarization the gas attains in relaxed thermal equilibrium. In an external magnetic field of value B of the experimental set-up $P_{Boltzmann}$ is connected to the Boltzmann constant k, the absolute temperature T and the magnetic dipole energy—$\mu_I B$ by the eq.

$$P_{Boltzmann} = \tan h(\mu_I B_I/kT) \quad (1)$$

Highest magnetic fields are being used in medical MR scanners, but still $P_{Boltzmann}$ is <<1 and hence can be calculated in good approximation as $P_{Boltzmann} = \mu_I B/kT$. Typical values in scanners are B=1.5 T and T=300 K. Consequently, a ³He polarization would attain only a value of $P_{Boltzmann}$ 3.9·10$^{-6}$, whereas values $P \leq 1·10^{-2}$ are necessary in order to compensate the loss of signal which is due to the much lower atomic density in the gaseous phase as compared to tissue. Gases with such high polarization degrees are termed also "hyperpolarized". Their preparation is performed by known procedures, preferably by optical pumping (OP). In spite of the high polarization degree one has to provide relatively large quantities of hyperpolarized gas for the applications; for instance a quantity of order 0.5 to 11 is necessary per patient for studying lung ventilation.

The quality of the gas as tracer substance in MRT is measured by its polarization degree because the contrast of an MRT-image increases linearly with the polarization degree. At each excitation of nuclear resonance, the polarization vector is being flipped out of the axis of the magnetic field by a so-called flip angle ($\alpha$). Through each of these excitations, the actual value of the hyperpolarization P is being irreversibly reduced to the value P.cos $_\alpha$. Aspiring a given image contrast, the flip angle may hence be chosen the smaller, the higher the value of P is in order to keep the product P.sin $_\alpha$ which determines the signal strength constant. A higher polarization enables therefore a larger number of excitations with one and the same bolus of tracer gas. This offers the possibility to increase per tracer bolus either the spatial resolution or the number of images acquired at spatial resolution or the number of images acquired at constant spatial resolution. The latter is particular important for functional lung studies for which totally new sources of information are being opened by the application of hyperpolarized ³He gas. Such methods are described for instance in the publications:

W. G. Schreiber, K. Markstaller, B. Eberle, H.-U. Kauczor, N. Weiler, R. Surkau, G. Hanisch, M. Thelen;

"Ultrafast MR-Imaging of Lung Ventilation Using Hyperpolarized Helium-3"; Eur. Radiol. 9, (1999) B28, A. J. Deninger, B. Eberle, M. Ebert, T. Großmann, W. Heil, H.-U. Kauczor, L. Lauer, K. Markstaller, E. Otten, J. Schmiedeskamp, W. Schreiber, R. Surkau, M. Thelen, N. Weiler; "Quantification of regional intrapulmonary oxygen partial pressure evolution during apnea by $^3$He MRI"; im Druck in J. Magn. Res. (November 1999), X. J. Chen, H. E. Müller, M. S. Chawla, G. P. Cofer, B. Driehuys, L. W. Hedlund, G. A. Johnson; "Spatially Resolved Measurements of Hyperpolarized Gas Properties in the Lung in vivo. Part I: Diffusion Coefficient"; MRM, in press (June 1999).

On the other hand, one may also reduce at higher P the amount of tracer gas necessary for reaching a given image contrast in order to minimize the alteration of normal lung ventilation, according to viscosity and diffusivity of ordinary air, by the admixture of $^3$He. The smaller the tracer bolus, the more realistic and valuable are the data end results. In producing nuclear spin polarized gases, one has to pay attention, therefore, not only to the yield, but in particular also to a high polarization degree.

There is a problem, however, to achieve high polarization degrees, for instance P>30%. Here the method of optical pumping of an alkaline vapor (mostly rubidium) followed by a spin polarization exchange between polarized alkali atoms and unpolarized $^3$He atoms may be applied. Such procedures and applications are described in the following publications:

B. Driehuys, G. D. Cates, E. Miron, K. Sauer, D. K. Walter and W. Happer; "High-volume production of laser-polarized $^{129}$Xe"; Appl. Phys. Lett. 69:12 (1996) 1668–1670, Thad G. Walker, William Happer; "Spin-exchange optical pumping of noble-gas nuclei"; Review of Modern Physics 69:2 (1997) 629–642, K. C. Hasson, P. L. Bogorad, B. Driehuys, G. Kameya, B. Wheeler, and D. Zollinger; "Polarized Helium-3 Production and Transportation System"; Eur. Radiol. 9 (1999) B16, further descriptions can be found in WO9640585A1 vom 19.12. 1996: "Method and System for producing polarized $^{129}$Xe Gas", WO9639912A1 vom 7.6. 1996: "Coatings For Production Of Hyperpolarized Noble Gases", U.S. Pat. No. 5,545,396 vom 8.13. 1996: "Magnetic resonance imaging using hyperpolarized noble gases", U.S. Pat. No. 5,557,199 vom 17.9. 1996: "Magnetic resonance monitor", U.S. Pat. No. 5,612,103 vom 18.3. 1997: "Coatings for production of hyperpolarized noble gases", U.S. Pat. No. 5,617,860 vom 8.4. 1997: "Method and system for producing polarized 129 Xe gas", U.S. Pat. No. 5,642,625 vom 1.7. 1997: "High volume hyperpolarizer for spin-polarized noble gas", U.S. Pat. No. 5,789,921 vom 4.8. 1998: "Magnetic resonance imaging using hyperpolarized noble gases", U.S. Pat. No. 5,785,953 vom 28.7. 1998: "Magnetic resonance imaging using hyperpolarized noble gases", U.S. Pat. No. 5,809,801 vom 22.9. 1998: "Cryogenic accumulator for spin-polarized xenon-129", U.S. Pat. No. 5,860,295 vom 19.1. 1999: "Cryogenic accumulator for spin-polarized xenon-129".

The most powerful apparatus of this kind, is described in Hasson et al (1999) (s. above); it achieves a $^3$He yield of e.g. 2 bar l/h at P=10% or 0.38 bar l/h at P=30% or 0.11 bar l/h at P=40%.

An alternative procedure, the direct optical pumping of $^3$He in a low pressure discharge followed by compression, achieves high polarization, at present for instance P>30%, and simultaneously high yields, e.g. 0.5 bar l/h (equivalent to 12 bar l/d). For that $^3$He gas is taken from a reservoir and nuclear spin polarized by absorption of circularly polarized laser light at λ=1083.2 nm within a gas discharge at a pressure of 1 mb. Compressed thereafter and stored, the polarized gas is at disposal for various purposes in fundamental physics research as well as for medical applications. This procedure is described in detail in the following publications:

G. Eckert, W. Heil, M. Meyerhoff, E. W. Otten, R. Surkau, M. Werner, M. Leduc, P. J. Nacher, L. D. Schearer; "A dense polarized $^3$He target based on compression of optically pumped gas"; Nucl. Inst. & Meth. A 320 (1992) 53–65

J. Becker, W. Heil, B. Krug, M. Leduc, M. Meyerhoff, P. J. Nacher, E. W. Otten, Th. Prokscha, L. D. Schearer, R. Surkau; "Study of mechanical compression of spin-polarized $^3$He gas"; Nuc. Instr. & Meth. A (346) (1994) 45–51

W. Heil, H. Humblot, E. W. Otten, M. Schäfer, R. Surkau, M. Leduc; "Very long nuclear Relaxation times of spin polarized helium 3 in metal coated cells"; Phys. Lett. A 201 (1995) 337–343

R. Surkau; "Entwicklung und Test eines $^3$He-Neutronen-Spinfilters"; Dissertation an der Johannes Gutenberg-Universität Mainz (1995)

R. Surkau, J. Becker, M. Ebert, T. Großmann, W. Heil, D. Hofmann, H. Humblot, M. Leduc, E. W. Otten, D. Rohe, K. Siemensmeyer, M. Steiner, F. Tasset, N. Trautmann; "Realization of a broad band neutron spin filter with compressed, polarized $^3$He gas"; Nuc. Instr. & Meth. A 384 (1997) 444–450

W. Heil, H. Humblot, E. W. Otten, M. Schäfer, R. Surkau, M. Leduc; "Very long nuclear Relaxation times of spin polarized helium 3 in metal coated cells"; Phys. Lett. A 201 (1995)337–343

R. Surkau; "Entwicklung und Test eines $^3$He-Neutronen-Spinfilters"; Dissertation an der Johannes Gutenberg-Universität Mainz (1995)

R. Surkau, J. Becker, M. Ebert, T. Großmann, W. Heil, D. Hofmann, H. Humblot, M. Leduc, E. W. Otten, D. Rohe, K. Siemensmeyer, M. Steiner, F. Tasset, N. Trautmann; "Realization of a broad band neutron spin filter with compressed, polarized $^3$He gas"; Nuc. Instr. & Meth. A 384 (1997) 444–450.

The state of the art is described in the publications Surkau (1995), Surkau et al (1997) and R. Surkau, A. J. Deninger, J. Bermuth, M. Ebert, T. Großmann, W. Heil, L. Lauer, E. Otten, J. Schmiedeskamp; "Highly polarized $^3$He for Lung MRI"; Eur. Radiol. 9 (1999) B15.

The state of the art polarizer comprises five sections:

1) Gas is delivered from a gas delivery unit
2) The nuclear spins are then polarized at pressures between 0.5 mb and 5 mb in a polarization unit
3) A compression unit then compresses the gas to a final pressure of up to 10 bar
4) A storage unit stores the polarized gas for an extended period of time for the purpose of transport and application.
5) The units which contain polarized gas have to be embedded in a homogenous magnetic field, a prerequisite for sustaining the polarization over extended periods of time. A typical field strength of 0.8 mT is being applied for instance.

That magnetic field has to fulfill a certain limit of homogeneity. Let the relative, transverse field gradient $G_r$ fulfill for example the limit $$G_r = \partial Br/\partial r/B_0 < 5*10^{-4}/cm. \quad (2)$$

Then one achieves at pressures of e.g. 200 mb or more which occur e.g. in storing gases still a gradient induced longitudinal relaxation time of $T_{1G} > 47$ h. Here one has used the relation $$T_1 = (p/G_r^2 * 17000) h/(bar\ cm^2), \quad (3)$$

given in the publication:

L. D. Scherarer, G. K. Walters; "Nuclear Spin-Lattice Relation in the Presence of Magnetic-Field Gradients"; Phys. Rev. 139:5A (1965) 1398–1402

G. D. Cates, S. R. Schaefer, and W. Happer; "Relaxation of spins due to field inhomogenities in gaseous samples at low magnetic fields and low pressures"; Phys. Rev. A 37 (1989) 2877–2885.

In order to achieve within the relevant region the necessary homogeneity, required above for preserving the polarization, the magnetic field is formed by five circular coils of equal diameter with ampere turns number and relative distances to each other suitably adapted. The two outer coils on each side are being arranged cylindrically with respect to the central coil. All five coils are connected in series in order to maintain a uniform current in au of them. The correct relative ampere turns number is then adjusted for each coil by choosing the suitable turns number. This procedure has the advantage that the relative contribution of each coil to the total field remains constant even in case of small current drifts. Hence, a homogenous field is formed reliably within the volume of the coil arrangement.

The gas delivery assembly comprises a $^3$He reservoir and a sluice which takes periodically gas from the reservoir and delivers it to a purification stage. This way, a $^3$He flux is formed which is being purified from contaminant gases ex other noble gases. Here, one uses highly porous getter material ST 707, supplied by SAS, Milan. The first stage, at a temperature of about 250° C., absorbs predominantly molecules by cracking them to atoms and binding these atoms. In a second stage at room temperature, the getter material diminishes the par pressure of hydrogen to very low values, i. e. hydrogen is adsorbed in the getter effectively. Thereafter, the purified gas is guided through a capillary and a liquid nitrogen trap into the assembly for optical pumping. The capillary establishes by means of a pressure gradient a continuous flow into the polarizing unit. On the other hand, it prevents a back diffusion of polarized gas into the purification unit and into regions outside of the homogenous field, where the polarization would be destroyed quickly.

The polarization unit comprises four cylindrical, 1 m long and 75 mm wide cells (320). In these cells, high frequency fields power a gas discharge at pressures between 0.1 and 3 mb and produce metastable $^3$He gas ($^3$He*). This $^3$He* absorbs resonant light at $\mu$=1083.2 nm from a suitable light source (for instance, cw Nd:LMA solid state laser). This light is being circularly polarized by polarization optics and irradiated parallel to the external magnetic field. The angular momentum which is transferred by light absorption to the atoms is orienting the nuclear spins parallel or antiparallel to the magnetic field axis depending whether the light polarization is right or left handed. For details on the physical processes see the relevant literature e.g.:

F. D. Colegrove, L. D. Schearer, K. Walters; "Polarization of 3He Gas by Optical Pumping; Phys. Rev. (132) (1963) 2561–2572, P. J. Nacher and M. Leduc; "Optical pumping in $^3$He with a laser"; J. Phys. (Paris) 46 (1985) 2057–2073.

G. Eckert, W. Heil, M. Meyerhoff, E. W. Otten, R. Surkau, M. Werner, M. Leduc, P. J. Nacher, L. D. Schearer, "A dense polarized $^3$He target based on compression of optically pumped gas"; Nucl. Inst. & Meth. A 320 (1992) 53–65.

After passing a cell once, the laser beam is reflected by a dichroitic mirror, thus giving the light a second chance for absorption. Fluorescence light from the discharge at $\lambda$=668 nm is transmitted, however, by the mirror. The degree of circular polarizaton of this fluorescence light is being measured and transformed via pressure dependent gauge factors into the a absolute degree of nuclear polarization by means of a polarizaton monitor which is described in the publications:

N. P. Bigelow, P. J. Nacher, M. Leduc; "Accurate optical measurement of nuclear polarization in optically pumped $^3$He gas"; J. Phys. II France 2 (1992) 2159–2179

W. Lorenzon, T. R. Gentile, H. Gao, R. D. McKeown; "NMR calibration of optical measurement of nuclear polarization in $^3$He"; Phys. Rev. A 47:1 (1993) 468–479.

More details are given below. The cells are connected in series. So the gas is flowing slowly through the cells and gaining steadily polarization.

After passing another liquid nitrogen trap, the gas enters periodically e.g. every ten seconds via an inlet valve into the compression volume of the first piston compressor. It is then compressed by a forward move of the piston and pushed via an outlet valve into a storage cell. The piston is driven by a linear drive, powered by compressed air. The lead through of the tappet to the interior of the compressor which meets ultra high vacuum standards is tightened by a bellow welded to the rear flange of the cylinder on one side and to rear end of the tappet on the other. All components of the compressor are made out of titanium or bronze in order to minimize polarization losses by wall contact with magnetic material. Said metals meet also ultra high vacuum standards and are wear and tear resist. The piston has a diameter of 140 mm and a stoke of 110 mm; it is tightened and guided by double lip O-rings. The intermediate storage is usually filled up to 200 mb before a second, in principal identical compressor compresses the gas to final pressures between 1 and 10 bar. The second compressor has a piston diameter of 60 mm and a stroke of 94 mm; it empties the intermediate storage by 6 consecutive compression cycles with a period of also 10 s.

The gas, highly compressed by the second compressor stage is pushed out into the storage cell, flanged to the compressor. This storage cell an be closed by its own valve and taken off the polarizer for transport. Such transportable cells are also used for long storage of the polled gas. An exemplary design for medical application is being built from a suitable, ironfree and diffusion resistant Supremax glass from the company Schott Glass, Mainz. In such cells, relaxation times of up to 100 h can be achieved. Moreover, the relaxation time may be prolonged further by help of a suitable coating of the inner surface. Up to 200 h relaxation time have been achieved that way, being described in the publications:

W. Heil, H. Humblot, E. W. Otten, M. Schäfer, R. Surkau, M. Leduc; "Very long nuclear relaxation times of spin polarized helium 3 in metal coated cells"; Phys. Lett. A 201 (1995) 337–343

W. Heil, J. Dreyer, D. Hofmann, H. Humblot, E.-Levievre-Berna, F. Tasset; "³He neutron spin-filter"; Physica B 267–268 (1999) 328–335.

The method of optical pumping of $^3$He in a low pressure discharge followed by compression has been well investigated theoretically. Yet it is still a great and many-sided physical and technical challenge to derive from these principles devices and to develop them to maturity such that the requirements regarding yield and polarization degree as well as reliability and guarantee of quality are met. Production, storage and subsequent transport of the hyperpolarized gas to the client requires innovative procedures and devices. Therefore, hyperpolarized gas was produced hitherto on a small scale only. Construction and operation of an apparatus for efficient production of highly polarized $^3$He gas demanded expertise in various fields of atomic and laser physics, in nuclear magnetic resonance, in ultra-high vacuum techniques, in handling special materials like Titanium or glass, for instance. Particularly in the case of clinical applications many different applicants at different places have to be supplied with gas of guaranteed quality.

Quality management can be realized best if the gas is produced in central facilities by specialists with powerful apparatuses. The polarized gas is then stored and delivered to the client.

SUMMARY OF THE INVENTION

The task of the invention is therefore to describe a production procedure and design which is based on the method of direct optical pumping of $^3$He and which guarantees that at equal final polarization an improvement of the yield by about one order of magnitude, as compared to the state-of-the-art, is achieved. The procedure comprises a number of principles in order to reach simultaneously the high yields and final polarizations. The principal task is to compress $^3$He gas, which has been nuclear spin polarized before to the highest possible degree, with as little polarization loss as possible. The higher investment cost of an apparatus which is required in using the method of direct optical pumping of $^3$He, as compared to the method of polarization by spin exchange, is tolerable because the production potential of the former is much higher due to physical laws limiting the potential of the latter.

An important aim of the invention is the sealing of moveable lead-throughs into the $^3$He gas volume. In this context one has to point out that in those parts of the apparatus which contain $^3$He gas the tightness and the characteristics of release of contaminant gases within the recipient have to meet ultra high vacuum (UHV) standards. Admixtures of contaminant gases of the order of ppm already considerably deteriorate the plasma conditions necessary for efficient optical pumping, and hence the achievable final polarization. Moreover, one has to use long-lived valves with an especially adapted design regarding cross-sections and volumes, made from non-magnetic or only weakly magnetic materials. The same holds for the compressor.

Moveable lead-throughs into the vacuum are realized most preferably by linear drives because this is the technically simplest solution. An UHV compatible lead through of a linear movement from the outside into the $^3$He gas volume has been realized hitherto with the help of highly elastic metal bellows which form a vacuum-tight connection between the moveable and the static part. Suitable bellows may be fabricated from Tombak or bronze in the form of wavy bellows or from titanium in the form of a membrane bellow. They all have in common a limited lifetime, defined as a maximum number of stretchings or pressings with a given travel, depending on the number of waves or membranes and on the geometric design. Thereafter fatigue failures cause breaks and consequently leaks in the material. The aspired number of stretching or pressing cycles lies in the order of several hundred thousands up to several millions. According to the desired travel, this requires very bulky and costly realizations of the bellows.

According to a first, essential idea of the invention a method according claim 1 is described which solves the problem of sealing moveable lead-throughs into the $^3$He gas space in a manner which saves space and costs and which establishes for all dimensions a reliably working principle of a UHV compatible linearly moving lead-through. A moveable component is moved linearly within a housing. Here the moveable component separates a first space which is in conducting connection with the outside from a second space which is in conducting connection with a closed system. This closed system comprises the polarized gas. In doing so, the moveable component is designed in such a manner that in between the first and the second space an intermediate space is formed, the purpose of which is to avoid to a high degree the infiltration of contaminant gases from the outside into the closed system.

According to another idea of the invention this intermediate space is evacuated through a pumping connection in order to pump out, with high guarantee, any gases leaking from the outside into the intermediate space such that they cannot enter into the closed system. This principle of sealing with selective pumping of intermediate volumes is called "fractional pumping" in the following.

This design of an assembly leading through a linear movement into closed systems in an UHV compatible manner can now be used advantageously for the realization of compressors and/or valves. In case of compressors, the moveable component is a piston, which displaces by its movement the compression volume and compresses thereby a medium inside that volume. In case of valves, the moveable component is the tappet which serves to interrupt the connection between two openings in the housing of the valve.

The length of the element, e.g., the UHV compatible lead through can be chosen such that the extension of the intermediate space is always larger than the travel of the moveable component. Thereby, one excludes with advantage that any medium from the outside is adsorbed to those surfaces of said UHV compatible lead through which will be part of the surface of the closed system after the movement of the moveable component. Thereby one avoids that contaminant media are brought in via intermediate adsorption to the surface of said UHV compatible lead through.

Since in general several of such UHV compatible lead throughs, consisting each of a housing, a moveable component and an evacuated intermediate space may be used in one device, these housings may be gathered to a single one, comprising several moveable components such that the intermediate spaces are conductively connected to each other. From this results advantageously a space-saving design characterized in particular in that all intermediate spaces can be evacuated via a single pumping connection.

According to a further idea in this context, one uses sealing materials which are placed within notches around the piston or the tappet or its counterparts. These sealing materials comprise, for instance, sliding gaskets formed as O-rings, giving rise to a most efficient separation of said spaces from each other and still allowing for a movement of the pistons or the tappets.

In applying such, e.g., UHV compatible lead throughs, in facilities for the production of polarized $^3$He gas, one has to make sure that an external, homogenous magnetic field is not being distorted and that the surfaces show as few paramagnetic centers as possible, in order to achieve and to maintain high polarization degrees. Moreover the surfaces themselves should not release any contaminant gases in order not to affect the efficiency of the fractional pumping. Therefore, housings, moveable components and sealing materials which are in direct contact or coming close to polarized $^3$He are built from materials with outgassing rates as low as possible and which are not or only weakly magnetic.

In addition to the above mentioned qualities, surfaces which are passed by slide seals should exhibit in particular a sufficient abrasion resistance. With preference, one uses materials like titanium or bronze for that purpose.

As has been said already, one employs for the above described compressors with preference a long piston—it has to be longer than its travel length. In general this leads to a considerable increase of the total length of the compressor. In particular in case of long travels which are preferred in the described application, one achieves an advantage if the pressure chambers which hydraulically drive the compressor are integrated within the inner space of the piston, in order to shorten the overall length.

Moreover, the piston compressor and its drive must not distort the homogenous magnetic field. For a space-saving apparatus, therefore, the drive has to be placed close to the actual compressor and must be built from non-magnetic materials. Another idea of the invention is therefore the use of a hydraulic drive integrated within the tappet or the piston. The drive is built from the same materials also used for the compressor or the valve.

In order to reach at a given diameter of the piston the desired final pressure of e.g. 10 bar within the compression volume, the drive has to exert a sufficient force. With preference, one may use here hydraulic drives since at oil pressures of up to 250 bar typically, one needs only relatively small end-faces for the oil chambers within the piston or tappet, in comparison to the end-face of the $^3$He-filled compression volume. This way one can still exert the force necessary to realize the desired drive of the piston or tappet. Also for that reason the drive may be housed within the piston; in doing so one maximizes at the same time with advantage the stroke of the piston for a given maximum overall length of the compressor.

In order to enable a movement of the piston in both directions one employs, according to another inventive idea, two pressure chambers within the piston or tappet, such that through pressurizing one or the other chamber, the piston or tappet is moved into or out of the housing. At the same time, the oil is again driven out of the other, non-pressurized chamber. This way the direction of movement can be inverted as often as wanted. In particular, one may also drive the piston or the tappet into a position in between the extreme ones. These positions can also be stabilized after closing off the oil chambers. As long as the force exerted by the oil is larger than the forces which the gases within the closed system exert onto the piston or the tappet, the piston or tappet may be moved this way as wanted. In general this condition can always be realized for the application as $^3$He compressor.

In a variant of the here proposed principle of a compressor for extrapure gases, one may chose instead of a slowly running piston compressor with a larger compression volume and long stroke, described above, a fast running piston compressor which yields the same throughput at smaller compression volume and shorter stroke. Here the principle of fractional pumping via intermediate spaces will still be preserved. In this case, the drive of the piston may be realized advantageously in the traditional way by a crankshaft and a connecting rod.

Certainly one has to tolerate, in the case of a fast running piston, higher leakage rates through the gaskets, since hermetic sealings require a higher pressing to the surface which could lead at high speed to unbearable friction forces and friction heat. However, the ratio between leaking rate and the amount of compressed gas per unit of time does not increase in proportion to the leaking rate itself since, at the other hand, the compression time is shorter. This principle is known as "dynamic sealing". Anyway one must not tolerate for reasons of cost any leakage losses in compressing such rare noble gases as the isotopes $^3$He and $^{129}$Xe, considered here.

The principle of fractional pumping, described here, solves this problem in the following way which may be used for any system with evacuated intermediate spaces: An amount of noble gas which is leaking out of the closed system into the intermediate space is pumped out via a pumping connection. After separating off the contaminants, e.g. by cryogenic means, the purified noble gas can be recycled again.

According to another inventive idea the principle of fractional pumping, applied to a moveable lead-through into a gas-filled space, is now used for a device for nuclear spin polarizing $^3$He gas with the method of direct optical pumping. This device comprises the same functional assemblies as in the state-of-the-art:

a polarization assembly in which the $^3$He gas is nuclear spin polarized in a low pressure plasma at pressures between 0.5 and 5 mb;

a compressor assembly for compressing the polarized gas to final pressures up to 10 bar;

a storage volume in which the gas is stored for extended periods of time for the purpose of transport and application.

Implementing the above described fractional pumping advantageously leads to an essential increase in efficiency of the facility. This concerns in particular the preservation of the polarization—once it has been achieved—during compression.

Another inventive idea regards the support of the fractional pumping by the choice of raw materials with a low outgassing rate. Moreover it has to be considered, that with preference the entire vacuum tubing is placed within the homogenous magnetic field which is important for the process of polarizing. In order to maintain field homogeneity the tubing has to be made of iron-free materials. In general one may therefore chose aluminum as raw material for tubings. Knife-edge rings from aluminum may be used as seals here. These aluminum knife-edge seals have the advantage, compared to ordinary polymer seals (plastics, rubber like Viton, NBR etc.), in that they do not outgas more than the raw material itself; therefore, residual gas pressures below $10^{-6}$ mb are easily reached. Glass to metal transitions in the low pressure region of the apparatus are also sealed metallically using soft Indium. On the high pressure side, O-rings from Viton are being used. In comparison with all other polymers Viton is suited best because it has the tightest matrix and hence relatively small outgassing rates of contaminants like e.g. $N_2$, $O_2$, $CO_2$, or hydrocarbons.

For a system which is built and tightened in the described manner one observes in front of the pumping connection a residual gas pressure of less than $5*10^{-9}$ mb. This marks an important improvement in comparison to the state-of-the-art where all vacuum components are made of glass and hence only stop cocks of glass with small cross-sections (maximum diameter=5 mm) and hence small conductance could be used. The strategy of choosing large pumping cross sections supports in particular the method of fractional pumping.

Another inventive idea regards the extension of the principle of fractional pumping also to the region of the $^3$He plasma with the advantage of achieving better working parameters, such as higher gas throughput and higher final polarization. By use of gas-selective pumping, the region of the $^3$He plasma is purified from contaminant gases leaking in or desorbing from the walls. High purities of better than 10 ppm with respect to the concentration of contaminant gases are required within the optical pumping volume in order to reach densities of excited, metastable He atoms sufficient for efficient absorption of the optical pumping light. Atoms of contaminant gases will quench the excitation energy of He atoms during collisions. With preference one can introduce getter pumps in the process of fractional pumping for the purpose of selective purification of noble gases, since noble gases can neither be chemi- nor physisorbed. Provided the diffusion times to the getter surfaces are shorter than the flow times through the getter pumps, the probability of the contaminant gas being adsorbed is high due to the high affinity of the surface. Therefore, selective sorption pumps are advantageously suited for the purpose of further fractional pumping at the entrance or the exit of the optical pumping volume. This way the penetration of contaminant gases into the optical pumping volume is prevented effectively. Such contaminants can be released for instance from sealing materials within the compressor. Hence highest final polarizations and yields can be achieved by the use of getters.

One uses getter pumps which rely on physi- or chemisorption of gases at or within a mostly metallic matrix. Fresh and extremely pure metallic getter surfaces can be produced by evaporation or cathode sputtering in a vacuum, either steadily or in a suitable rhythm. Alternatively non-evaporable getters (NEG) are being used. Their porosity offers a large surface to volume ratio and hence a large capacity.

In the device according to the state-of-the-art, a NEG is employed consisting of pills of sintered metal powder; the alloy is ST 707 from SAES getters, Milan, Italy. This getter is used to purify gas entering from a storage unit. This alloy contains 5.4% of iron which acts strongly relaxing on the $^3$He polarization. In order to prevent the penetration of magnetic dust and hence of a strong source of relaxation into the apparatus, the getter material has been enclosed in the state-of-the-art in between glass frits with pore diameters ranging from 40 to 100 $\mu$m. Nevertheless there remains a residual risk of contamination with ferromagnetic dust in the state-of-the-art.

Therefore, a further inventive idea in this sense foresees the use of purification units with evaporation getters based on non-ferromagnetic getter substances in the device described here. For instance, one can use metallic Titanium as getter material; also metallic Bismuth is a well-suited getter material. A Titanium sublimation getter can be activated by heating a Titanium filament applying a high electric current. Thus reactive Titanium atoms are evaporated which form a reactive layer on the surface of the gas purification units, serving as an active adsorbent for vapors and gases other than noble gases. Freshly sublimated Titanium will be passivated by binding contaminant gasses; re-activation therefore always requires the evaporation of fresh Titanium. The necessary evaporation rate corresponds to the amount of contaminants entering per unit of time. In order to dispose of a sufficiently large active getter surface for selective pumping, a fresh Titanium surface is deposited within suitable intervals of time.

Assuming for instance a tube diameter of several cm, a gas pressure of 1 mb, and room temperature, the average diffusion time to the inner wall which is covered by the getter will be of the order of 1 ms, at higher pressures accordingly longer. The dwelling time of the gas within the getter, where it has to be purified, should be at least one or two orders of magnitude longer than this average diffusion time. When one activates the evaporation of Titanium one observes in fact, even at pressures of 40 mb, that spectral lines other than those of He are bleaching out in the spectrum of the gas discharge instantaneously.

Other getter materials like Cesium or Rubidium show similar sorption qualities as Titanium or Bismuth. However, alkali metals are more volatile at room temperature and react chemically with polymers which are used as sealing materials.

Titanium and Bismuth, as well as Cesium and Rubidium, have in addition the property of acting only weakly relaxing on $^3$He. A Bismuth coating of glass cells leads to a decisive increase of the relaxation times in the storage volume up to 50 hours due to its diamagnetic character. Using Titanium or Bismuth getters avoids the danger that e.g. magnetic particles which stem from the use of porous ST 707 material in the state-of-the-art are spreading as aerosols within the apparatus. Therefore, one can go without separating the regions of Titanium or Bismuth getters by glass frits from the volume containing polarized $^3$He. Thereby one can ensure a strong diffusive contact of gas with the getter material and hence a good purifying performance. Such Titanium or Bismuth evaporation getters can be characterized in the following generally as non-magnetic evaporation getters.

In choosing raw materials and actual design of volumes which carry polarized gas, one has to consider that highest final polarizations and highest yields can be reached only if the polarization, once generated, is well-preserved. This is equivalent to the demand of minimizing the relaxation which is dominated by wall relaxation. The wall-related relaxation rate $\Gamma_W$ increases linearly with the ratio of the surface (S) to volume (V)

$$\Gamma_{1,W} = 1/T_1 = \gamma_W S/V. \tag{4}$$

There $\gamma_W$ is the specific relaxation coefficient of the surface. Therefore, one first of all has to choose the right material.

For devices for spin polarizing $^3$He gas by the method of direct optical pumping one uses with preference glass, Titanium and Aluminum. For sealing one may use Indium, oxygen-free copper rings and Aluminum rings, depending on the particular place of deployment. To a very limited extent and with minimized dimensions one may also use rubber O-rings made of Viton or NBR for sealing valves, for instance. All of these materials are non-magnetic and preserve the homogeneity of the external holding field. In the region of the $^3$He plasma one uses with preference only metallic sealing materials as mentioned above. Surfaces in contact with slide seals are made of abrasion-resistant Titanium, as in the case of valves or the compressor, for instance. However, they can also be made of bronze, in particular phosphorous bronze, or chrome-plated bronze. These materials are also characterized by sufficiently long relaxation times for polarized $^3$He. Cells for collecting or storing polarized $^3$He are made of weakly relaxing glasses. They can be well evacuated with efficient removal of contaminants like relaxing oxygen. On the other hand they show little wall relaxation and hence are suited for long-term storage of polarization.

Besides featuring materials with low specific relaxation coefficients, the above described evaporation getters have the advantage of forming small gas volumes with a minimal intrinsic surface, i.e. a small S/V ratio in comparison with porous, also non-magnetic sorption getters (for instance charcoal or so-called molecular sieves, i.e. highly porous silicates). In contrast to the usual sorption pumps which display huge active surfaces due to their porous structures, one ensures in the case of a Titanium getter a sufficiently large active surface by its mode of operation. Adsorbed contaminant gases or vapors are covered up with a fresh Titanium layer and retained that way. Hence evaporation getters are suited as selective sorption pumps for further fractional pumping in the region of polarized gases like $^3$He, for instance. In particular one may use Titanium or Bismuth getters also as purification units in the region of the polarized $^3$He gas itself.

Such non-magnetic evaporation getters for fractional pumping can also be employed as a purification unit in between the storage unit of the gas and the optical pumping volume, as a kind of pre-purifier in order to minimize the amount of contaminant gas stemming from the storage unit. This way one can achieve a maximum density of metastable atoms in the gas discharge and hence maximum values of the final polarization.

With preference one employs several fractional pumping stages. Within an extended optical pumping volume one may employ at least one purification stage, for instance at the connecting pipeline in between two partial volumes. In the case of limited diffusion, caused e.g. by a higher gas pressure, the efficiency of the method is increased that way. In addition one can first guide $^3$He gas from a storage unit into a first purification unit. After a sufficient dwelling time therein, a valve to the optical pumping volume is opened, which comprises at least one additional purification unit at the entrance of this volume, as described above. This unit has the purpose to retain penetrating impurities (contaminant gases) and to perform a post-purification of the gas.

If sorption getters are in direct diffusive contact with the $^3$He plasma, then the efficiency of the sorption getter can be increased further with advantage by applying a negative voltage, with respect to the plasma, to the sorption area, turning it into a cathode. Atoms of contaminant gases have a lower ionization potential than He and hence are preferentially ionised. In the electric field, positively charged ions will drift particularly fast to the sorption areas.

Another idea of the invention regards the increase in efficiency of sorption getters by cooling the adsorbing surface, for instance by means of a liquid nitrogen trap. Whereas the cold trap can be designed as a cold finger, the sublimation getter will consist for instance of a helical Titanium filament wrapped around the finger. The finger is cooled down to 77 K by filling it with liquid nitrogen and, therefore, will freeze out gases with low saturation vapor independently even of the getter substance. Dominant among these gases are hydrocarbons, carbon dioxide, and water vapor. By cooling the active metal surface, the binding of volatile gases like nitrogen and oxygen and, in particular, hydrogen is still more effective.

Whereas polarization degrees of at least 50% can be achieved at gas pressures of 1 mb by preparing well the optical pumping cells, the polarization degree can be raised further by the help of these additional gas purification units. Thereby, the coated finger or the titanium evaporation getter may be activated individually or simultaneously. In particular, they block-off contaminant gases arising from the compressor or its valves by diffusion, and thus guarantee long running times without loss of polarization efficiency.

As has been pointed out the design of pipelines and vessels containing polarized gas is essential for preserving the polarization effectively—besides the choice of suited materials with the a small value of $\gamma_W$.

All pipelines carrying polarized gas have a relatively large surface to volume ratio (S/V) and, therefore, act as relatively strong sources of relaxation according to eq. (4) as compared to the wide spaces in the volumes of optical pumping, of the compressor and of the storage cells, for instance. It is a general demand, to keep the residence time ($\tau$) of a certain gas bolus in a particular volume short as compared to the relaxation time $T_1$ characteristic for that volume, such that the polarization after passing this volume $$P(\tau)=P_o \exp(-\tau/T_1) \approx P_0 \qquad (5)$$

is still close to the original one before entering that volume.

A particular demand is to keep the volume of the gas feeding system $V_f$ (tubes, valves) small in comparison to the total gas bolus $V_{cy}$ which is put through within one compression cycle of period $\tau$. In a discontinuous mode of putting through the gas which is practiced in this device advantageously, the gas at rest for most of the cycle time $\tau$. Then, according to the above described inventive thought, the fraction of gas $V_f/V_{cy}$ which is exposed for the time $\tau$ to the relaxation rate $\Gamma_{1f}=1/T_{1f}$ of the dead volume of the piping system, will be minimized. On the other hand, surface relaxation which occurs within the piping system during the relatively short time of pushing through the gas in the discontinuous mode can be neglected already if relaxation times $T_{1f}$ of several minutes are reached therein. Therefore, the aim is to minimize the volume $V_f$ of the piping system.

This aim is realized best—also with regard to the conductance for viscous and molecular flow—by designing the pipelines as short as possible. In most cases, however, a minimal length l is predetermined already by needs of the construction. For large fluxes, the radius r=d/2 (compare eq. 18 below), has to be chosen large; but this way the volume of the pipeline increases which ought to be as small as possible, on the other hand. This requires an optimized spatial coordination of the different functional units with respect to each other. In compromising between the necessary conductances for viscous and molecular flow on one and the dead volume on the other side, the radii r must still be chosen scanty, since the dangerous surface to volume ratio scales only with r, but the dead volume (of a tube) with r squared.

Using a piston compressor for compressing gases, one has to observe a few general, important functional parameters which also play an important role in designing the dimensions of the pipeline. Let us call the product of the cross section of the piston and of the stroke of the piston the stroke volume $V_{str}$. In an exemplary realization a stroke volume of 50.3 l has been chosen. This is to be related to the volume $V_{f1}$ of the feed tube from the optical pumping region; in the example given, a ratio $\kappa_e = V_{f1}/V_{str} = 0.0062$ has been reached. It has been reduced a lot as compared to the value $\kappa_e = 0.10$ of the foregoing version; this means an improvement since any relaxation losses of the incoming gas in this region do not reach a relevant level anymore.

In the forward position of the piston at maximum compression, there is still a residual volume in the compressor which we call its dead volume $V_{c,d}$; it includes the volume of the feed lines to the valves. We define an effective compression factor $K_{eff}$ as the ratio of the outlet pressure $p_{out}$ which the compressed gas obtains in the forward position of the piston when being pushed out and the inlet pressure $p_{in}$ which the gas attains in the backward position of the piston after having been let in:

$$K_{eff} = p_{out}/p_{in} \tag{6}$$

We also define a compression factor by construction $K_o$ as a ratio of the stroke volume to the dead volume of the compressor:

$$K_0 = V_{str}/V_{c,d}. \tag{7}$$

In the exemplary design $K_0 = 10.000$ has been reached. The inequality:

$$K_{eff} \leq K_o \tag{8}$$

holds. Equality is reached in case that during the compression phase also the outlet valve remains closed or that the pressure within the recipient at the outlet has reached a maximum value $p_{out} = K_o p_{in}$ which the compressor can deliver by construction. Then one calculates the relative fraction $\epsilon$ of gas which has been sucked into the compressor but not pushed out again after compression and hence remains in the dead volume of the compressor, to be $$\epsilon = K_{eff} V_{c,d}/V_{str} = K_{eff}/K_0 \tag{9}$$

$\epsilon$ reaches the value of 1 at $K_{eff} = K_0$; at that point the amount of gas being pushed out has shrunk to zero.

This circumstance has to be considered in particular in designing the feed tube between compressor and storage cell, the volume of which we call $V_{f2}$. With increasing outlet pressure, which means increasing $K_{eff}$, the volume $V_{out}$ of the gas bolus pushed out is shrinking. Hence, the ratio $$\kappa_{out} = V_{f2}/V_{out} = V_{f2}/(V_{str}(1/K_{eff} - 1/K_0)). \tag{10}$$

(which ought to be small) is rising. In an exemplary realization $V_{str} = 15.3$ l and an outlet feed volume of $V_{f2} \approx 8$ cm$^3$ has been achieved for the first compression phase of the buffer cell.

Inserting these numbers and $K_0 = 10.000$ from eq. (7) into eq. (10) one arrives for typical effective compressions of $K_{eff} = 200$ and $K_{eff} = 500$, respectively, at ratios $\kappa_{out} = 0.1$ and $\kappa_{out} = 0.27$, respectively. State of the art is $\kappa_{out} = 0.5$ and $\kappa_{out} = 2.5$, respectively (with $V_{f2} = 3.5$ cm$^3$, $V_{str} = 1.87$ l and $K_0 = 800$). Hence, the fraction $\kappa_{out}$ which is kept for a cycle time $\tau$ within in the feed out tube has been greatly reduced in the exemplary design of the invention, which is a result of the much larger stroke volume with the feed out tube being small. In the second compression phase up to several bars starting from a few 100 mb these considerations play a much smaller role since at these small effective compression factors, being in the range of 10 to 100, $\kappa_{out}$ in the range of $10^{-2}$ or even below.

The dead volume $V_{c,d}$ within the compressor is the most dangerous source of relaxation in the compression cycle since the gas therein faces a surface to volume ratio which is a thousand times larger as in the full stroke volume. Hence, the surface relaxation time $T_{1W}$ is a thousand times shorter according to eq. (4). It hence approaches the cycle time $\tau$ of typical 20 s or may be still much shorter in case of an unfavorable $\gamma_W$. Therefore, one has to take into account that this fraction of gas, given by eq. (9) might be fully relaxed before it is mixed into the fresh gas of the following cycle and fed eventually together with that into a storage cell. It hence diminishes the transfer factor $\eta$ between the polarization at the outlet ($P_{out}$) and at the inlet ($P_{in}$), defined as $$\eta = P_{out}/P_{in} = 1 - \epsilon$$

to values $\eta < 1$. Since the procedure, starting from low pressure in the optical pumping volume $p \approx 1$ mb), requires large effective compression $K_{eff}$, one chooses pretty a large compression factor by construction $K_0 = V_{str}/V_{c,d}$. The dead volume results mainly from residual gaps ahead of the first piston ring and from a gold ring seal which seals the cylinder to its head. Hence, it scales with the circumference of the cylinder as $$V_{c,d} = 2\pi r \alpha. \tag{12}$$

A typical value for the coefficient $\alpha$ in the case of a double lip slide ring is $\alpha \geq 0.17$ cm$^2$ (depending on pressure). From equations (9) and (12) follows for $$\epsilon = K_{eff} 2\pi r \alpha/V_{str}. \tag{13}$$

At given stroke volume $V_{str} = \pi r^2 h$ the radius r should be kept small in favor of the stroke h, therefore, in order to minimize $V_{c,d}$ and thereby polarizaton losses. In other words, one requires to keep the ratio $$\beta = 2\pi r/V_{str} = (K_0 \alpha)^{-1} \tag{14}$$

of the circumference to the stroke volume of the compressor as small as possible at a given value of $\alpha$. For example $\beta$ values should remain at least below $\beta < \frac{1}{30}$ cm$^{-2}$, better below $\beta < \frac{1}{100}$ cm$^{-2}$, and with particular advantage $\beta = \frac{1}{300}$ cm$^{-2}$ should be reached. In an design, featuring a stroke volume of 15.3 l, one has chosen a long stroke of 1.0 m, therefore, which results in a value of $\beta = \frac{1}{350}$ cm$^{-2}$.

At first sight, a fast running compressor with a shorter stroke seems to have another drawback as compared to one with a longer stroke and same cross section: As has been argued above, a larger relative fraction of the admitted gas will be kept in the dead volume after compression. This case is therefore characterized by a large amount of gas imprisoned in the dead volume in comparison to the bolus transferred into the buffer cell or the storage cell; hence it is less favorable. As said above, one has to expect within the dead volume a much shorter relaxation time for reasons of its large surface to volume ratio. In case of the imprisoned gas being hyperpolarized this feature of a compressor with a short stroke will lead to relevant relaxation losses at least in case of small stroke frequencies. The higher stroke frequency of a smaller compressor, however, will even out this draw back at least by parts, since also the residence time in the dead volume will be shorter, accordingly, in the same sense as has been discussed above regarding leakage losses.

According to a further idea of the invention it is advantageous therefore, to aspire a timely opening of the outlet valve at the moment of pushing the gas out of the compressor into a storage cell. This means that the valve has to open exactly in that moment, when the pressure in the compressor has reached the same value as in the volume into which the gas has to be pushed out. If it opened too late, then an unnecessary large amount of gas would stay for an unnecessarily long time in the dangerous dead volume before being pushed out.

But also a premature opening of the valve has to be avoided. This would be the case if the piston would not yet have compressed sufficiently and hence gas under higher pressure in the storage cell could flow back into the volume of the compressor via the early opened valve. Although, the gas would be returned straight away with increasing compression, an unnecessary loss of polarization may happen by the forth and back flow through volumes with unfavorable, that means faster relaxing materials and/or unfavorable surface to volume ratios. One therefore employs with preference a valve which opens automatically at overpressure in the compressor. According to the invention, therefore, another adjunct tappet is fixed with some play to the tappet of the valve. Before the gas is going to be pushed out into the storage cell, the tappet of the valve is moved into an intermediate position only such, that the adjunct tappet still closes the valve by help of the overpressure in the storage cell. When the pressure in the compression volume surpasses finally the one in the storage cell, then the gas in the compressor volume pushes back the adjunct tappet and opens the valve. After the gas has flown out of the compressor, the tappet of the valve is moved into the most forward position in which it closes the valve by external force via the adjunct tappet. In order to suck the gas out a storage cell back into the compressor, the tappet of the valve together with its adjunct tappet can be moved into a position in which the opening of the valve is guaranteed.

By this procedure, indirect sources of polarization loss caused by untimely operation of valves are excluded. This procedure simplifies with advantage the processing of the compression cycle which otherwise would require an exact timing of all steps with tolerances in the order of ms. Such a strict synchronization cannot be reached by means of pneumatics and hydraulics used here.

According to a further idea of the invention the increased overall length of the compressor described above can be used for installing an extended optical pumping volume in parallel which may be divided up in addition into several slim tubes. The aforementioned method of polarizing the gas relies on the optical pumping process (OP). In case of the direct $^3He^*$-OP resonant laser light at $\lambda=1083$ nm is being absorbed by metastable $^3$He-atoms ($^3He^*$). The term "resonant" means that the spectral composition of the laser light fits to the Doppler-broadened $^3He^*$ absorption line. Otherwise, the light could not be absorbed and used. At pressures around 1 mb, one reaches only a $^3He^*$-density of the order of $10^{10}/cm^3$ within the $^3$He plasma. At this relatively small density of absorbers, only a small fraction of the irradiated laser power is absorbed along the OP-cell. Moreover, this fraction is decreasing fast with increasing polarization degree. For instance, at P=50% it has decreased by almost 1 order of magnitude already. Typically, one observes at pressures of 1 to 2 mb at P=0%, an absorption length $l_0$ of 3 to 5 m within which the laser power drops off by a factor e that means down to 36%. At polarization degrees of 50% one observes $l_0$-values of 15 to 20 m and at P=60%, $l_0$ will exceed 60 m.

Following the idea of the invention, the OP cells can be stretched very much, for instance to a length of 24 m at diameters of 5 to 7 cm, in order to achieve long absorption paths and to absorb as much laser light as possible. After one passage, the light is back reflected by a mirror such that for the case of using for example 5 cells, one reaches now an absorption path of altogether 24 m, being three times longer than the state of the art. This results in producing the highest possible number of polarized atoms per unit of time. With further advantage re-absorption of the emitted fluorescence light is minimized by the long stretching of the OP-cells on cost of their diameter at constant volume. This has to be aspired since under the circumstances given, the fluorescence light is emitted rather isotropically and strongly depolarized. The absorption of light with the wrong handedness has a very strong depolarizing action on the atoms, however.

The mirror for back reflection of the laser light is designed as a dichrotic mirror, highly reflecting at 1083 nm and highly transmitting at 668 nm. Thus, it is reflecting back the pumping light back the into the OP-cell; fluorescence light at $\lambda=668$ nm, however, can be transmitted through this mirror. The degree of circular polarization of this fluorescence light is measured behind this mirror by an optical polarization monitor. It can be converted instantaneously in an absolute value of the nuclear polarization degree in the cell by means of gauge factors. This standard procedure as well as the calibration factors are described in the publications:

W. Lorenzen, T. R. Gentile, H. Gao, R. D. McKeown; "NMR calibration of optical measurement of nuclear polarization in $^3$He", Phys. Rev. A 47:1 (1993) 468–479

N. P. Bigelow, P. J. Nacher, M. Leduc "Accurate optical measurement of nuclear polarization in optically pumped $^3$He gas"; J. Phys. II France 2 (1992) 2159–2179.

The degree of circular polarization of the fluorescence light emitted from the OP-cells along the optical axis is converted in the state of the art by a rotating $\lambda/4$ retardation plate into linearity polarized light whose direction of polarization then also rotates at the same frequency f. After passing a static linear polarizer, an interference filter and a collimator, the light is then converted into an electrical current signal by means of a photo detector, for instance a photo diode. The amplitude of this signal then shows a modulation at the frequency 2f. After amplification by a pre-amplifyer, the modulated fraction of the current is amplified further by a lock-in amplifier and rectified in a phase sensitive manner. The measured value is then stored. The unmodulated, average fraction of the photo current which corresponds to the unpolarized fraction of fluorescence light is being measured by means of a low-pass filter and its is value stored in addition. The ratio of both values is the sought for degree of circular polarization. Divided by the known pressure sensitive gauge factor, it indicates the degree of nuclear polarization.

According to an idea of the invention, a new variant of the procedure for determining the degree of circular polarization avoids advantageously rotating mechanical elements. This alternative design generates in proportion to the degree of circular polarization of the fluorescence light a maximum and a minimum voltage value. Their difference divided by their sum and by the pressure dependant gauge factor again indicates the degree of nuclear polarization. To that end the 668 nm fluorescence light passes first a static $\lambda//4$ retardation plate followed by a liquid crystal element, a linear polarizer, a 668 nm-interference filter and a collimator and is then detected by a photo detector and amplified. A square wave generator generates a positive or a negative voltage signal which turns the liquid crystal element at one of the two voltages into a $\lambda/2$ retardation plate; at the other voltage it remains neutral. This way the plane of polarization is periodically switched by 90° which causes the analyzer to transmit alternatingly the left or the right circular polarized component of the fluorescence light. Correlated to the control voltage of the generator, they are then stored as two different values of the measured signal. From these two values one can then calculate the degree of nuclear polarization as indicated above.

Besides the advantage of the absence of rotating elements, this analyzing procedure is characterized by its high stability and reliabiltiy since only electronic variables are being used. Both procedures described here are insensitive with respect to slight tipping of the optical axis. Another state of the art procedure which also manages without rotating elements uses instead of the static $\lambda/4$ retardation plate and the subsequent liquid crystal element a polarization splitting cube. It measures the thereby separated polarization components also by separate photo detectors and separate amplifier chains. The measured value sought for, which is the ratio of these two separately generated signals, reacts quite sensitively on any kind of misalignment, as for instance a relative drift of the coefficients of the light conversion of the two detection branches etc. But the new procedure quoted second place here, has the advantage, like the first one, of using the same detection channel for both polarization components—hence it is free of the quoted sources of systematic errors.

The yield of polarized gas can be optimized further if one divides the optical pumping volume into several compartments, each having the volume of the compressor $V_{str}$: If one admits first unpolarized $^3$He-gas into a cell and then switches on the resonant circular polarized 1083 nm laser light, then the nuclear polarization shows in the beginning a very steep rise of the polarization as a function of time. This rise flattens with increasing polarization and reaches finally an asymptotic equilibrium value. This value lies below 100% because of competing relaxation processes. In the absence of optical pumping these relaxation processes will cause an exponential decay of the polarization. The slower these polarization processes are, the stronger is the gain of nuclear polarization per unit of time under the action of optical pumping and the higher the equilibrium polarization will be. In the optical pumping region the following relaxation processes dominate:

Relaxation by exciting the gas in the plasma

Ionization

Formation of excimers and molecular ions

Emission of polarized fluorescence light

Relaxation by diffusion in between departments with different polarization.

According to eq. (17) (see below), the latter one plays a role of an additional, effective relaxation rate $\Gamma_{1diff}$. Wall relaxation and relaxation by diffusion through field gradients (compare eqs. (4) (2), (3) are playing a subordinate role in this regime.

Since even mechanically slow piston pumps with large strokes may reach cycling times below half a minute, it is advantageous to divide the optical pumping volumes into several compartments connected in series. Each compartment consists again of several long cells. Then, in a discontinuous mode of gas exchange, the gas from the "last" compartment with the highest polarization, respectively, will be transferred into the compressor and compressed. Gas from the before last compartment is transferred at the same time into the last compartment and can be pumped there up to highest degree of polarization, called also fractionate optical pumping. The first compartment is then receiving an equivalent bolus of unpolarized gas.

For instance, one may choose two compartments. In the first compartment the gas is being pre-polarized, in the second compartment it is then pumped to high final degrees of polarization. Hence, twice the cycle time $\tau$ of the compressor is being used for polarizing the gas.

If one compartment has been subdivided into several cells, then these individual cells should be operated under similar working conditions, that means, the irradiated laser power as well as the resulting polarization degree should be the same. Fulfillment of the latter condition can be supported by easy diffusive contact within one compartment, that means in between its respective cells. In order to enable also a fast gas exchange at high gas flux, the respective cells are connected to each other via short feed tubes. A long feed tube in between two different compartments on the other hand leads to reduced diffusive gas exchange and hence essentially de-couples both compartments. This way one avoids the high effort of installing an extra valve within the optical pumping section but still succeeds in minimizing additional relaxation by diffusion of differently polarized gases in between the compartments.

Let $$T_{diff} = l\, V/A\, D \tag{15}$$

be the average diffusion time between the compartments. It is characterized by the exchange of a fraction $(1-1/e) = 64\%$ of the gas form a volume V through a connecting tube of length l at cross section A within that time. $D=D(p, T)$ is the self diffusion constant of $^3$He at a given pressure p. Then the inequality $T_{diff} \gg \tau$ must hold with $\tau$ being the time of a compression cycle. Choosing for instance in between compartment one and two, each having a volume of 17.5 l, a connecting tube with l=60 cm and a cross section of A=3.1 cm$^2$ then eq. (15) yields a diffusion time constant $T_{diff}$=310 s at p=1 mb and T=300 K at which D (p, T) achieves the value of 1700 cm$^2$/s. Hence, the above inequality is fulfilled at $\tau$=20 s. The polarizaton difference $\Delta P = P_2 - P_1$ between different compartments is being equalize with the time constant $T_{diff}$ according to the differential equation $$d(\Delta P)/dt = -\Delta P/T_{diff}. \tag{16}$$

In the compartment with the higher polarizaton this diffusion is playing the role of an effective relaxation rate of the polarization.

$$\Gamma_{1,diff} = (1/P_2)(dP_2/dt) = -(1/2P_2)(d(\Delta P)/dt) = (\Delta P/2P_2)/\tau_{diff}. \tag{17}$$

Typical values are $P_1$=30% and $P_2$=50% which leads to values of about $\Gamma_{1,diff} \approx (1500\ \text{s})^{-1}$. This is a relatively weak relaxation rate in comparison to the one caused by the plasma which attains values in the region of $(500\ \text{s})^{-1} \leq \Gamma_{plasma} \leq (200\ \text{s})^{-1}$, depending on the strength of the plasma.

At times of the discontinuous gas exchange, on the contrary one has to provide a high flux. Assuming laminar flow, the flux $\Phi$ through a feed tube of diameter d at length l scales as $\Phi \propto d^4/l$ according to the Hagen-Poiseulle-Law $$\Phi = \pi d^4 (p_2^2 - p_1^2)/(256 \eta l). \tag{18}$$

$p_2$ and $p_1$ are the respective pressures, $\eta$ is the viscosity coefficient of the medium. The length has to be minimized again for reasons of maximizing the flux that means the maximum gas exchange per unit of time.

In between the cells of a compartment, one can realize a tube length of l=30 cm, for instance, being much shorter as compared to l=60 cm in the state of the art. The flux rises like the square of the cross section, reciprocal to this, the time needed for equalizing the pressure between the two volumes is shrinking. The volume increase of the feed tube scales only linear with its cross section, however. Hence, one can find a suitable cross section by choosing d=2 cm, for instance. Even at pressures $p_2$=1.2 mb and $p_1$=1.0 mb between optical pumping volume and compressor one achieves according to eq. (18) with $\eta(^3He)$=19.6.$10^{-6}$ kg/(ms) a large flux of $\Phi$=15 mb l/s into the compressor. Whereas the flux is rising with the square of the pressure $p_2$ in the OP-volume the transferred bolus of gas is rising only linearly with it. Hence, the chosen cross section of the feed tube is sufficient. The length of the feed tube in between the two OP-compartments has been chosen to be l=60 cm at the same cross section. Since the same bolus of gas is moved everywhere in the discontinuous mode of operation, the choice of a twice as long feed tube leads to a rise of the difference pressure between OP-compartment 1 and 2 by a factor of (roughly) $\sqrt{2}$. However, this does not effect the performance of the procedure.

A further idea of the invention regards an optimization of the procedure by adapting the diameter of the OP-cells to the given laser power and to the average polarization which is being reached in the respective compartment and to the absorption length which depends on this polarization.

This way, the volume of the first compartment may be divided up in two cells, the (equal) volume of the second compartment into three cells, for example. At equal length of the cells this requires an increase of the diameter of the cells in the first department by a factor $\sqrt{3/2}$ compared to the second. In order to achieve an optimum polarization, the volume of the cells is illuminated by laser light as completely as possible. This requires to blow-up the light beam in compartment one more than in compartment two. At equal light power irradiated into compartment one and two this leads to a lower light intensity in compartment one, for the example given, only $\frac{2}{3}$ of that in compartment two. At a lower average polarization in compartment one of 30 to 40%, for example, also the absorption length which is related to the polarization decreases to 5 and 10 m, respectively. This leads to an absolute absorption of laser power in compartment one being about equal to that in compartment two. Hence, the gain of polarized atoms per unit of time is about equal in both. In compartment two one meets at an average polarization of 50% an absorption length of 15 to 20 m. After having passed all cells of the respective compartment twice in series, the initial laser power has decreased by a factor of order e=2.7 in both cases. At the average polarization degrees met in the two compartments under operating conditions, both compartments are hence optimized towards an effective use of the laser light.

At given laser power the equilibrium polarization which can be reached in a OP-cell is determined ultimately by its diameter. The present invention aspires higher polarization values as compared to the state of the art. Therefore, the diameter of the cells has to be limited to 70 mm in compartment one and to 54 mm in compartment two. The resulting total volume is 35 l. The corresponding stroke volume of the compressor, adapted to the described mode of polarization, would be half of that, i.e. 17.5 l, close to that of 15.3 l chosen in the exemplary design. It is made sure this way that the cell diameters are adapted to the different levels of polarization on one side and that they have been chosen to be sufficiently wide for the case of high laser powers on the other. At very high intensity the optical transition rate and hence also the absorbed power run into saturation. This superfluous fraction of light power is then passing the cells without being used. The optimized design according to the invention, however, leads to an optimal size of the optical pumping volume such that the residence time of the gas therein and hence also its polarization degree are being maximized at a given through-put.

Cell dimensions as given above require to broaden and parallelize the laser beam which has to be circular polarized completely before entering the optical pumping volume. To that end it is advantageous to polarize the laser beam first linearly by a polarizing beam splitter cube of high quality, followed by a suitably adjusted $\lambda/4$ retardation plate which turns the polarization into a circular one. Then follows a telescope which blows-up the beam to the required diameter and forms an intermediate focus on the opposite mirror such that the cell volume is illuminated as much as possible. Hence, the beam has to be weakly convergent only. After having traveled forth and back a long way through the OP-cells, chosen to be two times 240 cm for instance, it is advantageous to re-collimate the beam by lenses before it is mirrored into a subsequent cell. Through such a sequence of beam forming lenses any contact of the beam with the walls of the cell is avoided even with a beam profile adapted to the fall width of the cell. While doing so, it is advantageous to form a beam waist at the place of the back reflecting mirror, this waist being properly adapted again to the width of the cell. Otherwise, reflection of light from the cylinder of the cell would reduce its degree of circular polarization and, therefore, act as an additional source of relaxation.

Advantageously, the telescope consists of a concave and a convex lens which leads to a short overall length, and also limits the divergence of the beam in between the two lenses to relatively small angles. In spite of the anti-reflection coating of the lenses one has to pay attention to the latter argument for reasons of maintaining the circular polarization of the light.

Advantageously, the laser beam is fed through all cells of a compartment one after the other in order to make use of the full absorption length offered by construction. This way, as much light as possible is used for pumping. In particular, with a beam counter propagating to the flow, the region of highest polarization and hence absorption probability is provided with the highest possible polarization rate.

The OP-cells are made of a suitable material which requires that at least the entrance and exit windows are transparent for light of wave length 1083 nm. In general, one prefers di-electric materials. This way, radio frequency fields, used for maintaining the helium plasma can be coupled into the cells by external electrodes. Advantageously, the cells are made out of glass, even more advantageously, out of robust Duran glass by (Schott-Glass) or Pyrex (Corning). In addition, glass can be evacuated and outgassed at high temperatures by which contaminant gases are removed from layers close to the surface. In addition, one may fill the cells with a few mb helium and run a strong radio frequency or microwave discharge which sputters residual contaminant gases from the inner surface of the cells which then are pumped off. Thus, the $^3He$ gas will not be contaminated anymore by other gases during the polarizing process which otherwise would outgas or being sputtered off the walls by the plasma. Consequently, one reaches in a pure plasma a maximum lifetime and density, respectively, of the metastable helium atoms. This is a prerequisite for achieving high equilibrium relaxation and polarization rates.

Alternatively, it is also possible to use nonmagnetic metallic plasma cells with transparent windows, however. The windows will then be sealed to the tubes by help of metal seals (for instance gold rings) which also sustain the heat during outgassing. For this kind of cells one uses internal electrodes for firing the plasma. Alternatively, one may also couple advantageously microwaves into such metallic cells which function as wave guides in this case.

In order to avoid absorption losses in the windows of the OP-cells they are made advantageously from glass showing optical quality, for instance ZKN 7 (by Schott Glass). This can be sealed advantageously to Duran glass via intermediate transition glasses. In another design they consist out of "Borofloat glass" which can be sintered directly to the front of Duran tubes, provided the respective surfaces are optically flat.

Advantageously, the polarization optics is also anti-reflection treated in order to avoid losses of light power by reflection at the entrance and exit surfaces. Furthermore it is advantageous to eliminate reflection at least at the outer surface of the cell windows in order to avoid the typical reflection loss of 4% at each interface.

Advantageously, reflection is also eliminated from the lenses of the telescopes. This serves not only to avoid reflection losses but also to maintain the polarization degree of the light. At focal lengths of −100 mm for the first and +300 mm for the second length, for instance, one calculates in case of reflecting lenses the transmitted light to be depolarized by 0.5% only. But the finally achievable equilibrium polarization responds very sensitively even on small admixtures of circularly polarized light with opposite sense (details are given in the publication by Eckert et al (1992), quoted above). In fact, no change of the equilibrium polarization could be observed in the exemplary design when the positions of the telescope and the polarization optics were interchanged. Hence, any depolarizing action by the telescope has been excluded. Placing the polarization optics in the wide beam behind the telescope, however, required a very expensive polarization optics having a large cross section adapted to the one of the cell.

The economic, small polarization optics, having a lateral length of only 20 mm, allow in combination with the telescope in the exemplary design advantageously to blow-up the beam to a cross section optimal for optical pumping, still maintaining full polarization.

Spurious contaminations by oxygen have to be avoided not only in the optical pumping section but also in the storage cells for the polarized $^3$He-gas, since the hyperpolarization would decay with a rate $\Gamma_{1,O2}$, being proportional to the partial $O_2$-pressure. According to B. Saam, W. Happer and H. Middeton; "Nuclear relaxation of $^3$He in the presence of $O_2$", Phys. Rev. A 52 (1995) 862–865. This rate it given at low temperature of 20° C. by the eq.

$$\Gamma_{1,O2}=1/T_{1,O2}=p_{O2}/(\text{bar } 2.40 \text{ s}). \tag{19}$$

According to that relation, the oxygen dependant relaxation time $T_{1,O2}$ would be limited already to 312 h at $p_{O2}=2.10^{-6}$ mb which still would correspond to ordinary high vacuum conditions. The corresponding relaxation rate of $\Gamma_{1,O2}=(312 \text{ h})^{-1}$ already would make a considerable fraction of an aspired total relaxation rate of less than $\Gamma_1=(100 \text{ h})^{-1}$. $T_1$ denotes the time interval within which the polarization will decay to a fraction of 1/e of its starting value according to a time dependant exponential law.

Preferably, several pump systems are employed in one device in order to separate the tasks of fractional pumping and of conditioning of the apparatus. By this precaution the diffusion of contaminant gases or vapors in between the respective vacuum regions of the apparatus is being avoided and highest gaseous purity in the volumes of optical pumping and of the storage of $^3$He secured. In this sense one has to discriminate the regions which contain $^3$He during regular operation of the facility from the intermediate volumes of the valves and the compressor and from the rear space of the compressor which is exposed to oil vapors out of the region of the hydraulic drive. Conveniently, the intermediate volumes of the compressor are being evacuated together with the intermediate spaces of the valves by one and the same pump. This design allows in addition a continuous evacuation of the intermediate spaces of valves and the compressor, independent of the need of evacuation of relevant $^3$He working volumes. Furthermore, the tubing system for the evacuation of the $^3$He working volume is never contaminated with gaseous inpurities from intermediate spaces of the valves and the compressor. This increases the reliability with which the required purity of $^3$He within the $^3$He working volume is reached and maintained in the long run. This is a prerequisite for a long, failure-free period of operation and, therefore, for high mean production rates.

BRIEF DESCRIPTION OF THE DRAWINGS

The invention will now be described with the figures discussed below, which should be seen as examples but in no way as restrictions.

Figure legends.

Figure 5A:
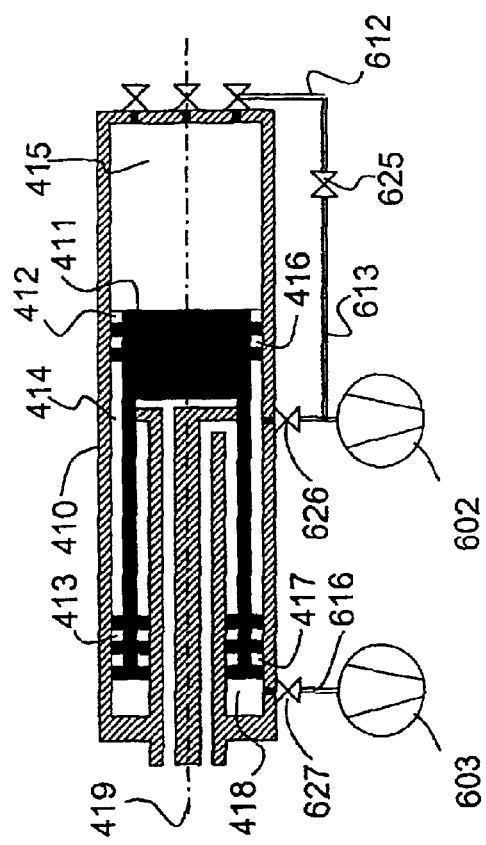
Figure 8A:
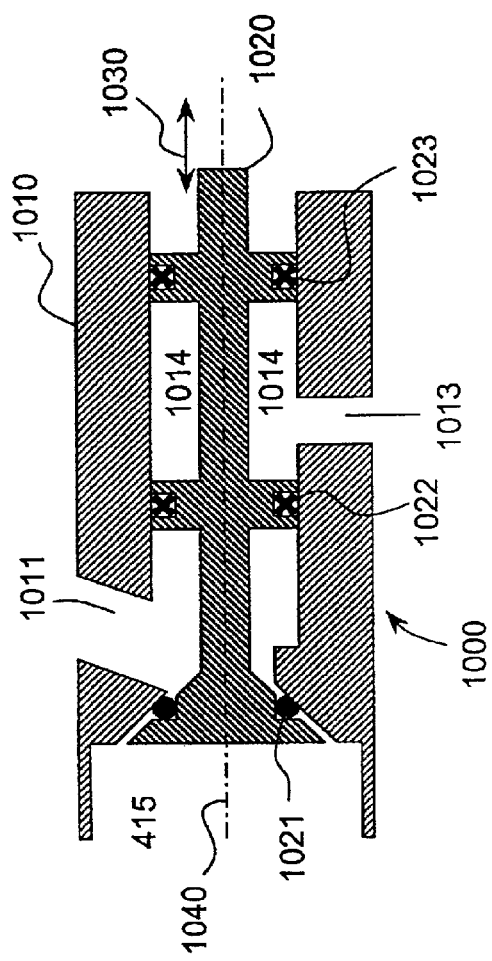
Figure 8B:
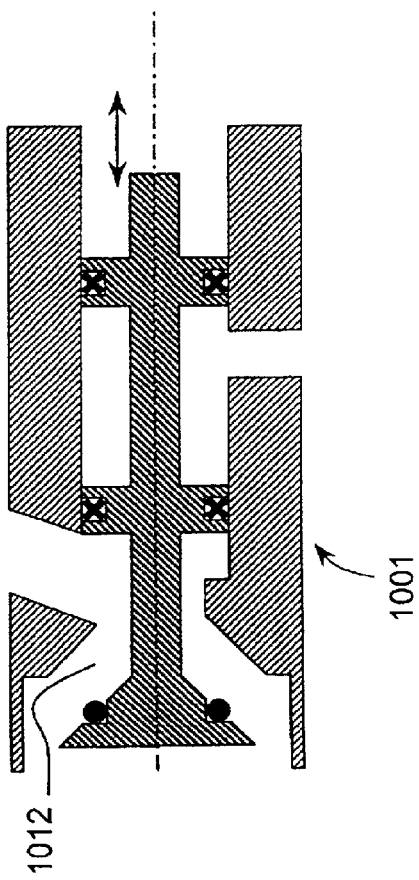
Figure 11:
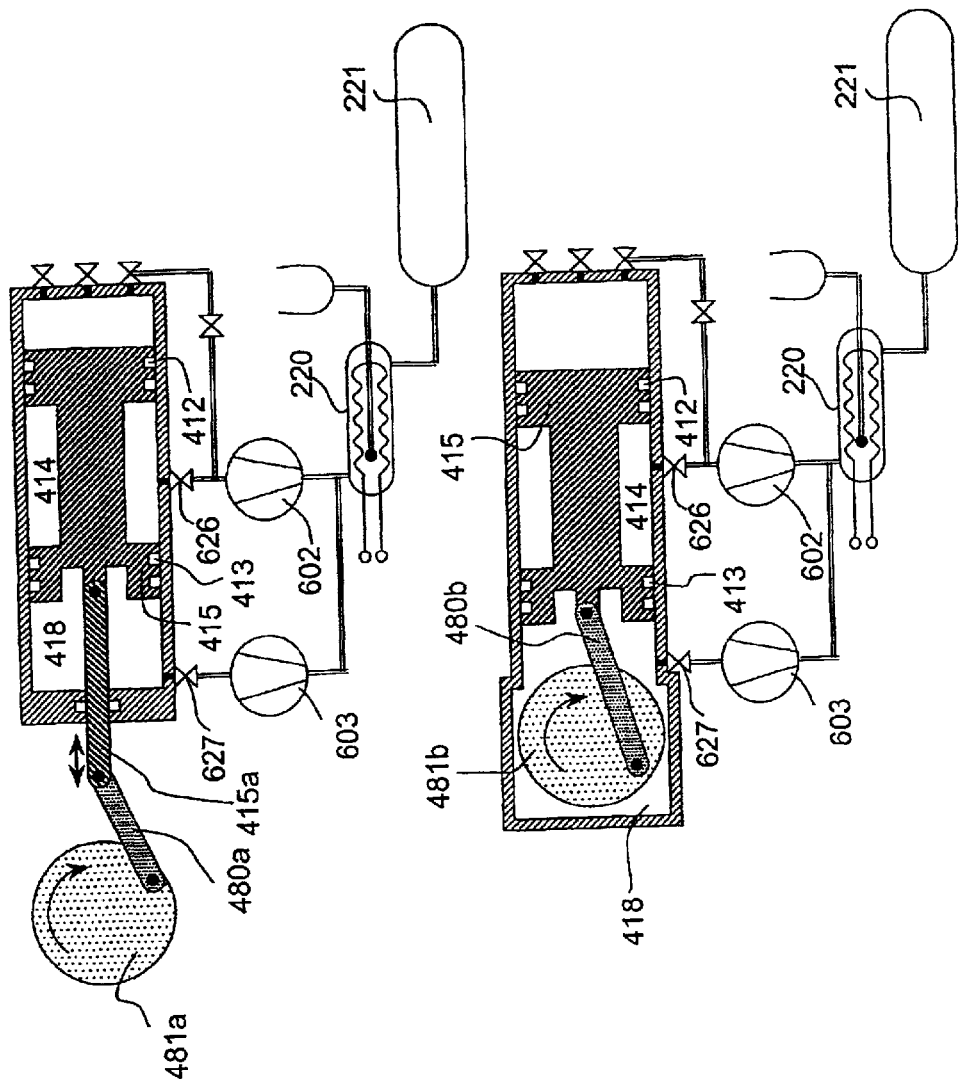

General scheme of the polarizer and compressor, based on the method of direct optical pumping of $^3$He according to the prior art;

FIG. 2:

General scheme of the polarizer and compressor, based on the method of direct optical pumping of $^3$He according to the state-of-the-art;

FIG. 3:

The elements of the polarizer and compressor described in the invention (based on the method of direct optical pumping of $^3$He) which are relevant for the polarization process;

FIGS. 4a,b:

Section of an UHV-compatible lead through described in the invention, featuring a moving component realized as a single valve, in closed and open position;

FIG. 4c:

Section of an UHV compatible lead through described in the invention, featuring several moving components realized as a group of valves, in closed and open position;

FIGS. 5a,b:

Section of an UHV compatible lead through described in the invention, featuring a moving component realized as single-stage piston compressor, with illustration of sealing gaskets and external pumping connection;

FIGS. 6a,b:

Section of an element described in the invention, featuring a moving component realized as single-stage piston compressor, with illustration of a double chamber hydraulic drive;

FIG. 7:

General scheme of the polarizer and compressor described in the invention, with an optimized pumping system;

FIGS. 8a,b:

Section of an UHV compatible lead through described in the invention, featuring a moving component realized as a valve, which is part of an assembly within the cylinder head of the compressor and serves as inlet valve and valve to the pumping connection. The valve is shown in closed and open position;

FIG. 9a–d:

Section of an UHV compatible lead through described in the invention, featuring a moving component realized as a valve, which is part of an assembly within the cylinder head of the compressor and serves as outlet valve. The valve opens automatically under over pressure, which is illustrated by drawings of different valve positions;

FIG. 10:

Maximum possible compression $K_0$ in dependence on the final pressure in a storage cell;

FIGS. 11a,b:

Fast moving piston compressors with smaller stroke volume and reduced stroke length. Two versions with outer and inner gear drive are drawn;

FIG. 12:

Temporal evolution of the $^3$He polarization in an optical pumping cell. The cell is first filled with unpolarized gas, then the resonant, circularly polarized 1083 nm laser light is coupled in;

FIG. 13:

Scheme of a part of the optical pumping volume, with polarizing optics, sequence of beam forming lenses and serial passage of the laser beam through two optical pumping cells;

FIG. 14:

Scheme of an apparatus to measure and analyze the circular polarization of the 668 nm fluorescence light, to determine the level of nuclear polarization of $^3$He. Drawn is (a) an old version and (b) a new version described in the invention;

FIG. 15:

Exemplary dependence of the attainable final polarization in optical pumping cells on the gas pressure of $^3$He. The two curves refer to different optical transition C8 or C9 of $^3$He*.

FIG. 16:

Temporal evolution of the $^3$He polarization in optical pumping cells, upon discontinuous or continuous replacement of gas;

FIG. 17:

Examples of the attainable polarization and the attainable quantity of polarized $^3$He gas, in dependence on the gas flux, utilizing the apparatus described in the invention.

DETAILED DESCRIPTION OF THE INVENTION

Figure 1:
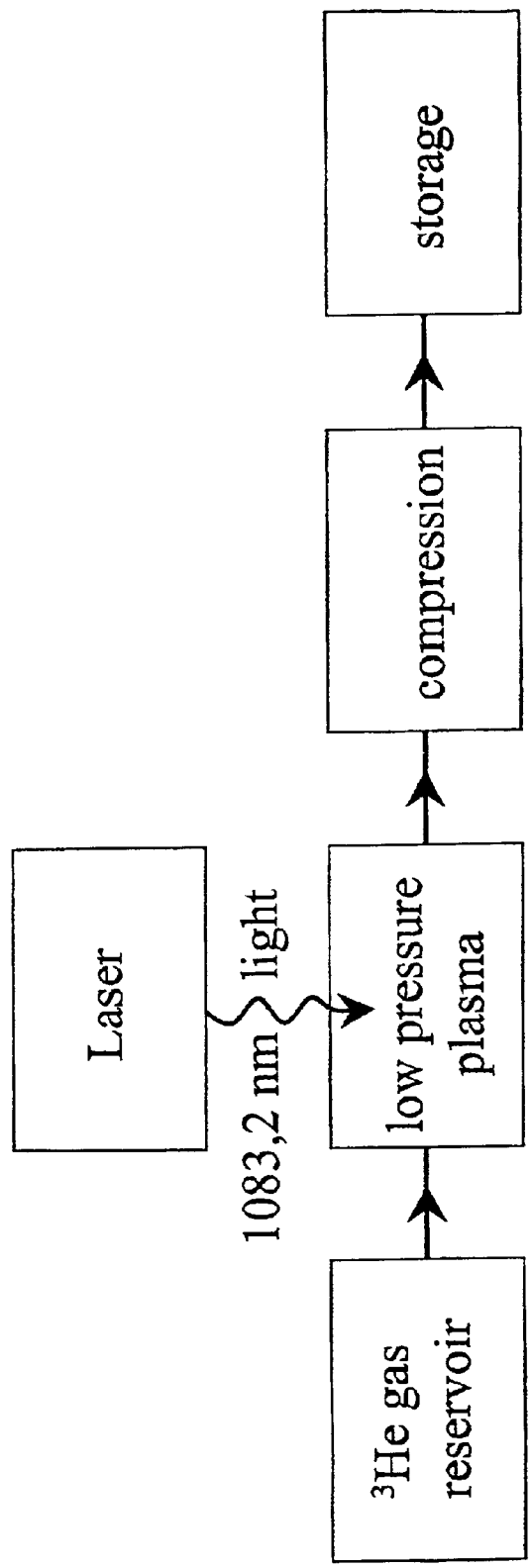
FIG. 1.

FIG. 1 sketches the provision of large amounts of nuclear spin polarized $^3$He, employing the method of direct optical pumping of $^3$He. $^3$He is extracted from a reservoir. At a pressure of ca. 1 mbar the gas is spin polarized in a plasma discharge by absorption of circularly polarized 1083.2 nm laser light. After subsequent compression and storage, the polarized gas may be utilized for different purposes, both in basic physics research and in medical applications.

Figure 2:
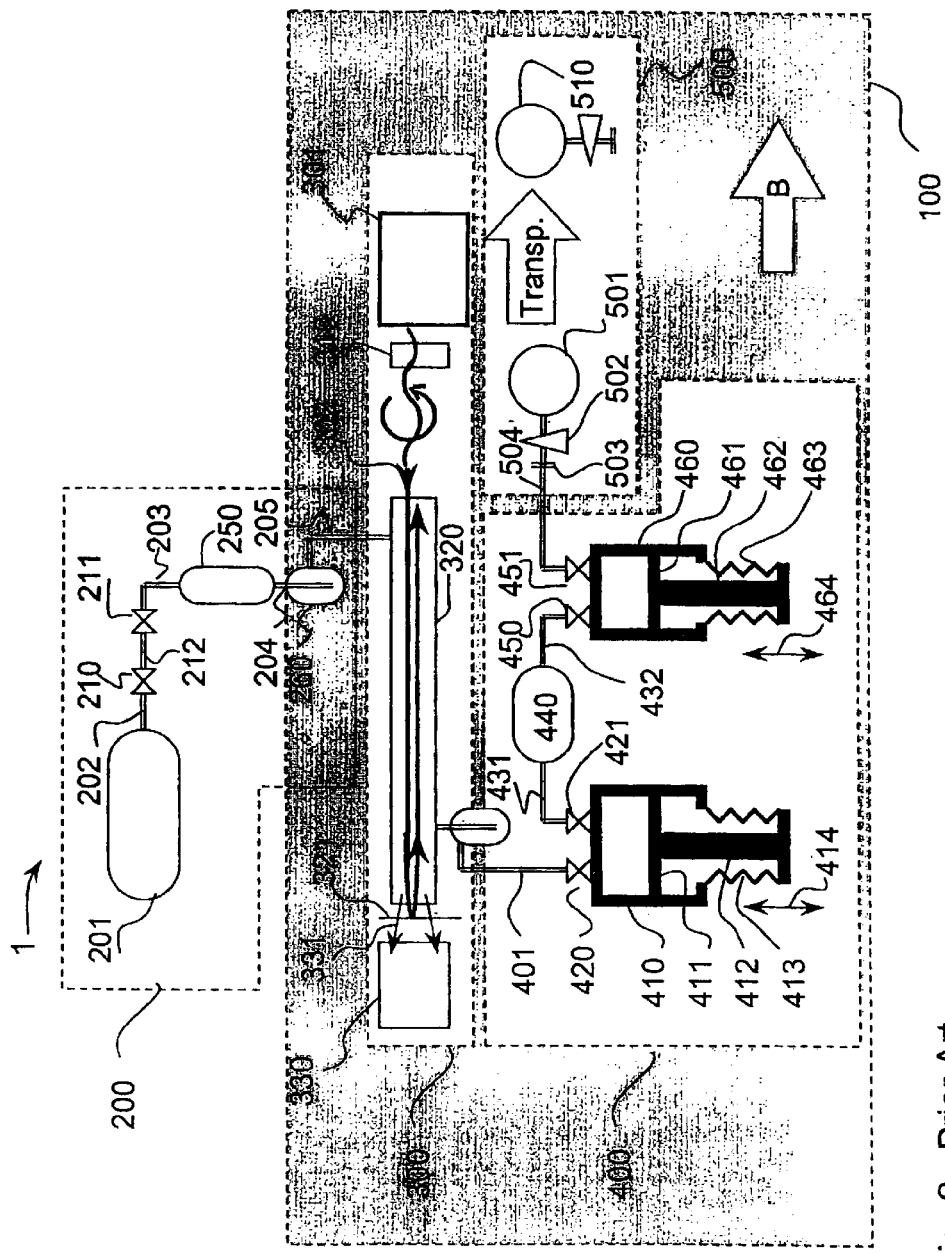

FIG. 2 shows the polarizer and compressor according to prior art techniques (1). It consists of 5 main assemblies: Gas is taken from a gas provision system 200, nuclear spin polarized at pressures between 0.5 and 5 mb in a polarization unit 300, compressed to final pressure of up to 10 bar in a compression unit 400 and finally stored in a joined storage unit 500 for some period of time during transport and application. A prerequisite to conserve the polarization for a long time is a homogenous magnetic field, assembly 100, embedding systems 300, 400 and 500 which produce and sustain the nuclear polarization. A typical magnetic field strength is 0.8 mT.

The magnetic field 100 consists of 5 circular coils of equal diameter, with suitable Ampère turns ratio and inter-coil spacing. The two outer coils on either side are arranged in an axially symmetric manner relative to the central coil. All 5 coils are in serial connection, to ensure an equal current in each coil. The necessary Ampère turns ratio is then adjusted individually for each coil according to the number of wire turns. The advantage of this approach is that the relative contribution of each coil to the total magnetic field remains constant, in spite of possible small drifts in the electric current. Thus a homogenous field area is produced within the coil volume which encompasses the apparatus.

The gas provision system consists of a $^3$He reservoir 201, which is connected via a pipeline 202 with a first valve 210. This valve, volume 212 and valve 211 form a sluice, which periodically extracts gas from reservoir 201 and releases it into the low-pressured pipeline 203. Thus a flux of $^3$He is produced. In the purification unit 250, the $^3$He gas is cleansed of gaseous impurities with the exception of noble gases. The purification unit utilizes highly porous getter material (St 707, SAES, Milan). In a first compartment, at a temperature of ~250° C., most molecules are absorbed, cracked into their atomic compounds and retained. In second compartment, at room temperature, the getter material reduces the hydrogen partial pressure to very low values, i.e. hydrogen is absorbed efficiently by the getter. The purified $^3$He gas flows subsequently through a capillary tube 204, a liquid nitrogen trap 260 and pipeline 205 into area 300. Via a pressure gradient, the capillary tube 204 generates a continuous flux of $^3$He into area 300. At the same time, this prevents a back-diffusion of polarized gas out of area 300 into the purification unit 250 and regions outside the magnetic field 100, where the polarization would be destroyed quickly.

Within the polarization unit 300, an applied electrical high frequency field ignites a gas discharge in 4 cylindrical cells 320 (length 1 meter, diameter 75 mm, gas pressure between 0.1 and 3 mbar), thereby creating metastable $^3$He gas ($^3$He*). The $^3$He* absorbs resonant 1083.2 nm light 302 from a suitable light source 301, e.g. a cw Nd:LMA solid state laser. The light is circularly polarized by polarization optics 310 and propagates parallel to the external magnetic field 100. The angular momentum conveyed by the absorption of light aligns the nuclear spin parallel (or antiparallel) to the magnetic field, depending on the right or left handed light polarization.

After a single passage through a cell 320, the laser light is reflected at a dichroitic mirror 321; therefore, non-absorbed light remains available during a second passage. By contrast, 668 nm fluorescence light passes through the mirror. The degree of circular polarization of this fluorescence light is measured by an optical polarization detector 330. Via some partly pressure-dependent gauge factors, this quantity is transformed into the absolute value of the momentary nuclear polarization. The cells are connected serially; the gas thus flows slowly through the cells and successively gains polarization.

Via another liquid nitrogen trap, connecting tube 401 and valve 420, the polarized gas is pipelined periodically (e.g. every 10 s) into the compression space of the first compression stage 410. A forward move of piston 411 pressurizes the gas, which is ejected via valve 421 into an intermediate storage cell 440. The piston is driven by a linear motor (sketched by 414), which operates with compressed air and conveys its movement via the end plate of the bellow 413 and the piston rod 412 to the piston within the ultra high vacuum tight compressor. All of the components 410 to 412 are made of titanium, in order to minimize polarization loss due to contact of $^3$He with magnetic wall material; furthermore, titanium is both suitable for ultra high vacuum applications and abrasion resistant. The piston (diameter 140 mm, travel length 110 mm) is sealed and supported by a "quad-ring" (Busak & Shamban). The intermediate cell 440 is usually filled to ~200 mb, before a second, basically identical compression unit 460 (with valves 450 and 451, piston 461 with diameter 60 mm and travel length 94 mm, piston rod 462, bellow 463 and drive 464) compresses the gas to a final pressure of 1 to 10 bar. The second compression unit carries out 6 compression cycles per filling maneuver, also with a 10 s period. Thus the intermediate cell is emptied to a minimal pressure $p_{min}$.

The gas, highly pressurized in the second compression stage 460, is pumped through the pipeline 504 into a storage cell 501, which is connected to a flange 503. The storage cell can be closed at the valve 502 and disconnected from the polarizer (1) for transportation. These transportable cells 510 are also used for Ia long-term storage of polarized gas. An exemplary model used for medical applications of $^3$He is therefore made of special Supremax glass (made by Schott Glas). which has a low iron content and a low Helium permeation rate. Within this glass vessel. $^3$He relaxation times of up to 100 hours can be achieved. In addition, by means of a suitable inner coating of the cells, the relaxation times may be prolonged and storage times of up to 200 hours can be achieved.

Figure 3:
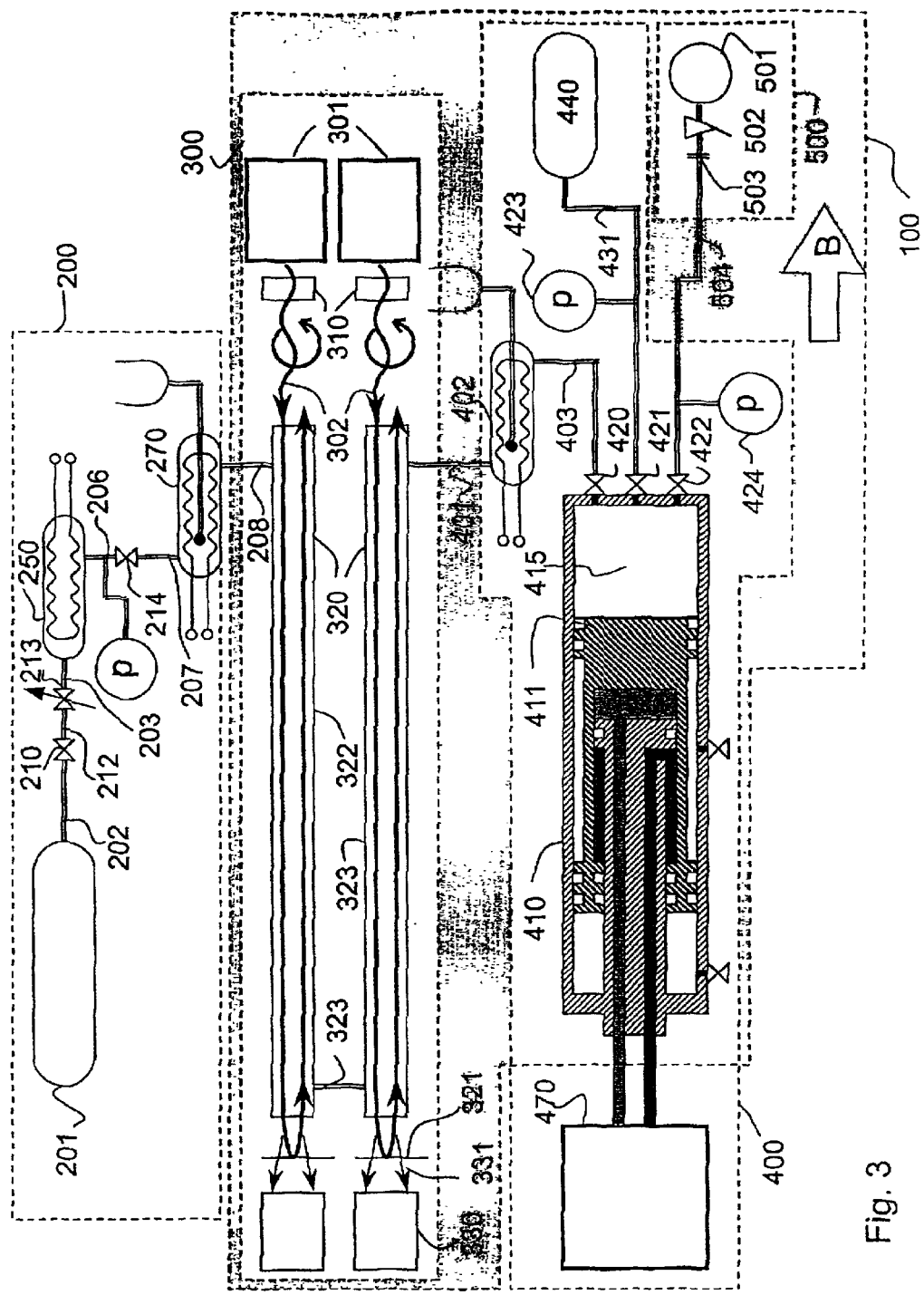

FIG. 3 depicts the elements of the polarizer and compressor described in the invention (based on the method of direct optical pumping of $^3$He) which are relevant for the polarization process. The gas provision system comprises a $^3$He reservoir 201, which is connected via a pipeline 202 with a first valve 210. The latter is connected via a pipeline 212 with a gas admittance valve 213. This valve regulates the gas flux f, so that over a time interval $\tau = q/f$ a desired gas quantity $q = p*V$ is filled into the volume V 250, until the desired pressure p is reached in the polarizing unit 300. The volume 250 contains a gas purification, realized as a titanium evaporation getter. Pure titanium is evaporated off a filament at gas pressures between 0 and 100 mb and condensed onto a surface, which then retains gaseous impurities with the exception of noble gases. Via a valve, pressure equilibrium with volume 320 can be established. Due to the lower pressure in 320, the bigger part of the gas quantity q is introduced into polarization unit 300. In between valve 213 and the polarization unit, another gas purification unit 270 is continually in contact with volume 320.

In this exemplary realization, the polarization unit 300 comprises several glass cells 320, which are 2.5 m long and connected serially by pipelines 323. Within the cells, an applied electrical high frequency field ignites a gas discharge at gas pressures between 0.5 and 5 mbar, preferably at ~1 mbar, thereby creating metastable $^3$He gas ($^3$He*). The $^3$He* absorbs resonant light 302 of wavelength λ=1083.2 nm from a suitable light source 301, e.g. a cw Nd:LMA solid state laser. The light is circularly polarized by polarization optics 310 and propagates parallel to the external magnetic field 100. The angular momentum conveyed by the absorption of light aligns the nuclear spin parallel or antiparallel to the magnetic field, depending on the right or left handed light polarization. After a single passage through a cell 320, the laser light is reflected at a dichroitic mirror 321; therefore, non-absorbed light remains available during a second passage. By contrast, 668 nm fluorescence light passes through the mirror. The degree of circular polarization of this fluorescence light is measured by an optical polarization detector 330. Via gauge factors, this quantity is transformed into the absolute value of the momentary nuclear polarization.

Via connecting tubes 401, 403, another gas purification unit 402 and valve 420, the gas flows into the evacuated compression space 415 of the piston compressor 410. A forward move of piston 411 pressurizes the gas, which is ejected via valve 421 or 422 and via pipeline 431 or 504 into an intermediate storage cell 440 or a storage cell 501. The latter can be closed by a stop cock 502 and disconnected from the flange 503 for transportation and/or application. The piston is driven hydraulically; the required oil pressure is provided by an aggregate 470.

If the relaxation time of the polarization (i.e. the time constant of the exponential decay of the hyperpolarization towards the Boltzmann polarization $P_B$ [eqn. (1)]) within the storage cell is sufficiently long, the disconnection of the storage cell from the filling apparatus described here is preferred, as preparation and application of the gas may be separated both spatially and temporally. This is a major advantage for the application of the gas, because the conditions for an efficient polarization of the gas (e.g. available resources, qualified personnel, adequately installed rooms, etc.) are usually not fulfilled at the location of application. This separation also opens up the possibility to efficiently prepare the gas at one location, while the user needs to concentrate on the application of the gas only. Thus a constant high quality at the location of production can be ensured, without restrictions upon the application of the gas.

Non-magnetic pressure gauges 423, 424 are preferably integrated along with the valves within the head of the compressor in this exemplary realization. Separately-housed pressure gauges, on the other side, would contribute to the dead volume of pipelines in an unnecessary way.

FIGS. 4*a* and 4*b* illustrate, with a scheme of a valve, a UHV-compatible linear movement lead-through which is cost-efficient, space saving and which, in particular, operates reliably in all sizes. FIG. 4*a* depicts a section of a closed valve (1000) and FIG. 4*b* a section of an opened valve (1001). In a preferred, easily manufactured design, the valve is made rotationally-symmetrical to the symmetry axis 1040, except for the valve drill-holes 1011 and 1013.

Within the valve housing 1010, a tappet rod 1020 is moved in a linear way by an external drive 1030. At closed position, the tappet closes off the connection between the valve drill-holes 1011 and 1012. Advantageously, a slide seal, e.g. a gasket ring 1021 made e.g. of rubber in form of an O-ring, preferably made of Viton, provides a sufficient seal, even at a pressure difference of up to 10 bar. Further gasket rings 1022 and 1023 separate the actual valve region 1011 and 1012 from a intermediate volume 1014 of the valve and the outer atmosphere 115 with valve drive 1030. These gasket rings may be preferably realized as two-lip seal rings. The intermediate volume 1014 is evacuated via the outlet 1013. This is accomplished e.g. via pipeline 612, valve 625 and pump 602 (FIG. 5*a*). From now on, this sealing principle, which involves selective pumping of intermediate volumes, is called "fractional pumping".

The pump 602 is preferably realized as an oil-free turbo molecular pump. An additional advantage of the gasket ring 1022 is the minimization of the actual valve volume between drill-hole 1011 and 1012. This is of special importance for the transport of hyperpolarized gas, as will be explained below. Furthermore, both gasket rings 1022 and 1023 serve to support the tappet rod.

This construction avoids an expendable and temperamental bellow as UHV separation between atmosphere and ultra-clean gas space. Air leaking in via gasket ring 1023 is pumped out via pump 602. The remaining diffusion of residual gas out of the intermediate volume 1014 via seal 1022 into the actual valve region 1011, 1012 is negligible and distinctly lower than the desorption from metal surfaces and gasket rings 1021 and 1022. An important feature of this construction, with regard to the aforementioned desorption rates, is, that the distance between the gasket rings that define the intermediate vacuum region is larger than the stroke of the tappet. Hence the parts of the inner valve surface that absorb gases outside the vacuum region cannot become part of the ultra-clean interior and re-desorb the adsorbed gases there. The gas transport via this adsorption-desorption cycle in the intermediate region is rather intercepted.

This valve construction requires little maintenance only; replacing the gasket rings is considerably cheaper than the exchange of bellows. The effort of operating a vacuum pump 602 especially installed for that purpose becomes necessary only once for all valves. With this pump, an arbitrary number of valves of this design can be evacuated. The joint intermediate vacuum region is controlled by a suitable vacuum display included as an operational security measure. This also guarantees safety in operation with respect to an unwanted entry of impurity gases. By contrast, a developing leak in a worn out bellow causes a failure without being detected readily.

As shown schematically in FIG. 4c, these valves are preferably grouped together as an assembly. In doing so, the intermediate volumes, e.g. 1014a and 1014b, are connected by a fine-pointed drill-hole 1013a and evacuated together via the pipeline 1013. Such a group of valves is preferably integrated within the head of the compressor. Further valves employed in the apparatus, for instance valves 624, 627, 629, 210, are also preferably grouped together. Thus, the accordingly designed valves, like e.g. 612 at drill-hole 1013, can be realized in a space and material saving manner, with short pumping distances and without a multitude of pipelines.

FIG. 5a shows the basic scheme of the compressor, realized as a piston compressor. The principle of the intermediate vacuum region, as discussed above with respect to the aforementioned valve design, is realized here, too. The piston 411 features gasket rings in notch 412 and 413 at the head and at the end, which define an intermediate region 414. Impurity gases or vapors which leak out of the rear volume 418 into the intermediate region 414, are pumped out via valve 626 and pump 602. Consequently, the transport of residual gas or vapor molecules into the compression space 415 via the gasket ring in notch 412 is not significant.

Another advantage is that the intermediate volume 414 is evacuated via a drill-hole within the cylinder and valve 626, and not internally via a possible drill-hole within the piston 411 with a subsequent vacuum line (e.g. a flexible hose). The design suggested here necessitates a piston length corresponding to the stroke length of the piston; however, the travel paths of the gasket rings in notch 412 and 413 do preferably not overlap. It is thus also obvious that the spacing between the piston rings is larger than the piston travel length.

Figure 5B:
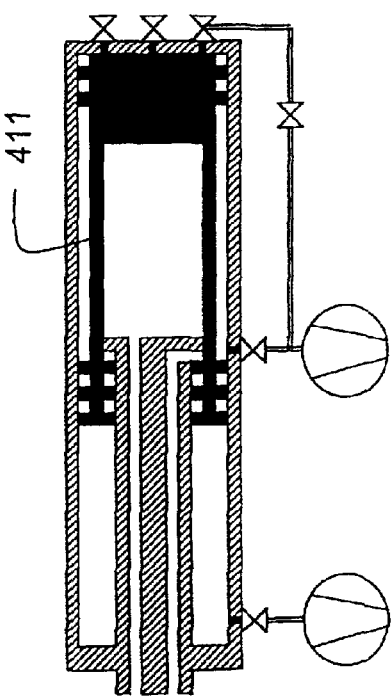

This design feature ensures that surfaces which, during movement of the piston, are in contact with, e.g. external air (e.g. within the rear volume 418) remain strictly separated from the ultra-clean interior due to the intermediate vacuum region. Hence the said entry of gas by means of an adsorption-desorption cycle is prevented. If the piston is pushed to front position (see FIG. 5b), impurity gas atoms, molecules or vapors within the rear volume 418 can be adsorbed by the walls; if the piston is pulled back, these atoms desorb off the walls. Once the gasket ring in notch 413 has passed, on its backward move, the position of the adsorbed impurity, the desorption takes place within the intermediate volume, and not within the actual compression volume 415. The impurity is likely to be pumped out via valve 625, before another adsorption (piston at front position) and desorption (piston at rear position) happens, which could lead to transportation into the compression space.

The gaskets of the piston are preferably realized as two-lip seal rings. They seal up the compression space 415 against the intermediate volume 414 and the rear volume 418. The pump 602 is preferably realized as an oil-free turbo molecular pump.

This principle—the interception of impurity gas entries by means of intermediate vacuum regions with movable vacuum lead in insulators—is hereinafter called "fractional pumping".

It characterizes the compressor described here as an "extrapure compressor". The same holds, equivalently, for valves and seals 1022 and 1023.

Gases and vapors emitted from the gear drive into the rear volume 418 are preferably pumped out already via valve 627 and pump 603. They stand hardly a chance to enter, by further adsorption-desorption cycles or by diffusion, into the ultra-clean interior. Therefore the constantly evacuated rear volume 418 and intermediate volume 414 both obey the principle of fractional pumping defined above. The region sealed up by the gasket rings in notches 413 and 412 thus establishes a double fractional pumping path. The pump 603 is already also realized as an oil-free turbo molecular pump.

Indeed, if the compressor is at rest, a pressure of $10^{-3}$ mb is reached within the rear volume 418, and $5.3*10^{-5}$ mbar within the intermediate volume 414. During operation, i.e. while the piston is moving, a pressure of $\sim 10^{-2}$ mb is found within the rear volume 418, and $1.1*10^{-3}$ mb within the intermediate volume 414. Even at the intermediate volume pressure of $1.1*10^{-3}$ mb, the diffusion of residual gas or vapor molecules out of the intermediate volume 414 via the gasket ring within notch 412 into the compression volume 415 is negligible, compared to the typical outgassing rate of the gasket rings. In this setup, the entry of gaseous impurities into the compression space 415 is reduced to a minimum (outgassing of the piston gasket ring within notch 412 and compressor material within chamber 415 itself), without utilizing an expendable bellow construction.

FIGS. 6a and 6b show a the scheme of the compressor. FIG. 6a depicts a section of the compressor, with piston 411 at rest position and maximum compression volume 415. In FIG. 6b, the piston 411 is moved forward, corresponding to the highest compression; the piston fills in the entire compression space. In a preferred, easily manufactured design, the compressor is made rotationally-symmetrical to the symmetry axis 419, except for the arrangement of valves in the cylinder head (for instance, 420, 421, 422 in FIG. 3 and valves 626, 627 in FIG. 5a) with corresponding drill-holes.

The piston compressor and its drive must not distort the homogenous magnetic field. Thus, in a space saving apparatus, the drive has to be made of non-magnetic materials and set up adjacent to the actual compressor. A preferred integrated, hydraulic drive with two pressure chambers was constructed for the exemplary realization; it is shown in FIG. 6a and FIG. 6b.

The piston, long for operational reasons—it has to be longer than its stroke length—generally leads to a considerable increase in length of the entire compressor. This is cumbersome, particularly in the case of a long travel length which is preferred in the application described here. This disadvantage can be overcome by a special hydraulic drive of the compressor, which integrates the pressure chambers within the interior of the piston itself; this drive is described below.

At first, the piston 411 is at rear position, as shown in FIG. 6a. For compression, oil is pressed out of the aggregate 470, through pipeline 471 and into the first chamber 472. Then the piston 411 moves towards the cylinder head of the compressor 410. Thereby, oil from the second chamber 474 is pushed back into the aggregate via pipeline 473 (FIG. 6b). When the compression procedure is finished (FIG. 6b), oil is pressed by the aggregate 470 into the pipeline 473 and the second chamber 474, thus moving the piston 411 back to the rear position. The notches 475 contain gasket rings suitable for hydraulic systems, which very tightly seal up the oil volume 474 against the rear volume 418. The notch 476 contains one gasket ring suitable for hydraulic systems, which seals up the first chamber 472 against the second chamber 474.

In order to build up the desired final pressure within the compression volume with a given piston diameter, the drive must exert a sufficient force. In the exemplary realization, a force in excess of 15400 N is required to accomplish a final pressure of 10 bar with a piston diameter of 14 cm. Advantageously, a hydraulic drive is utilized, since at oil pressures of typically up to 250 bar, only a small end-face area is needed for volume 472 to achieve this force (15.9 cm$^2$ in the exemplary realization). During the backward move, only the friction forces of the gasket rings must be overcome; a smaller end-face area of 5.7 cm$^2$ in the exemplary realization is sufficient for this purpose. Thus, the drive can preferably be situated within the piston, which serves to maximize the travel length of the piston at a given maximum external length of the compressor.

At the same time, two fractional pumping paths can be realized in a space saving way, as they are parallel besides the piston. Thus, bellows as high vacuum seals are made redundant.

This configuration preferably contains only a single moveable part, which is the piston 411. It is guided by rings within the notches 416, 418 and sealed by rings in the notches 412, 413, 475, 476. A possible breakdown due to elements connecting to external drives is therefore intercepted.

Furthermore, a hydraulic drive permits the placement of the piston 411 within the compressor 410 at any desired position. Thus, reduced stroke volumes $V_{red}$ may be adjusted, e.g. in order to compress a certain part of the gas into a storage cell 501 after establishing pressure equilibrium with the intermediate storage cell 440. This helps to save time, as a large intermediate storage cell can be filled up to an accordingly selected pressure, after which, successively, several small storage cells are filled with a dedicated quantity of gas. The gas quantity is adjusted, depending on the pressure in the intermediate storage cell, by the choice of $V_{red}$ via the rear position of the piston. As the mode of operation described below, which permits the filling of several storage cells arranged in parallel connection, also saves time required for evacuation, this method leads to an increase in mean production rates.

Figure 7:
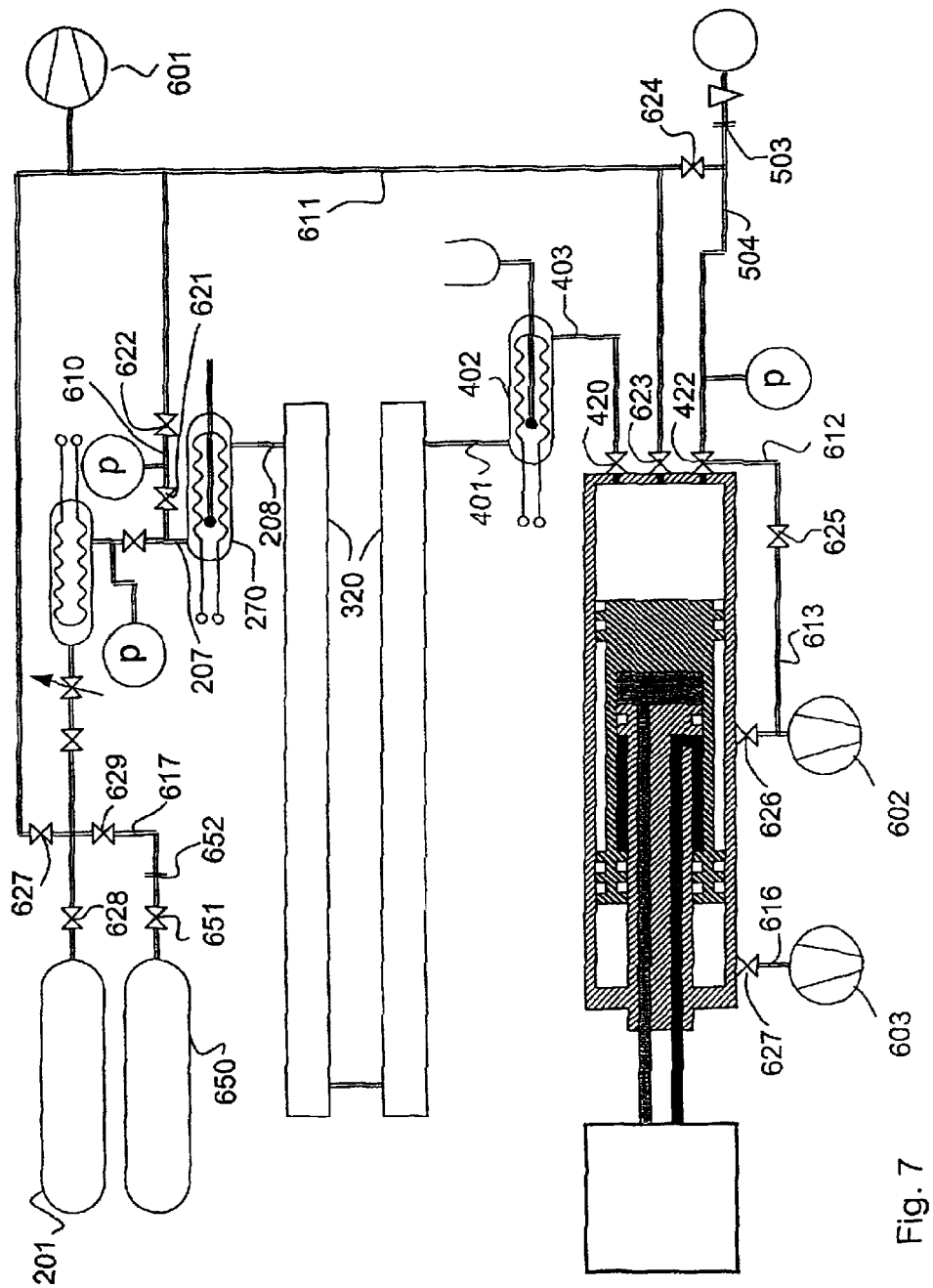

FIG. 7 shows a scheme to achieve good vacuum conditions, which are a prerequisite for high gas purity. Advantageously, three turbo pumps are used. Pump 601 serves for preparation of the apparatus. This encompasses the evacuation prior to the inlet of $^3$He and the filling of a storage cell, as well as the preparation of the optical pumping volume.

In order to fill $^3$He into the apparatus, a bottle 650 with valve 651 is connected to the flange 652. Air trapped in volume 617 is then pumped out by the pump 601 via valve 629, valve 627 and the tubing system 611. Afterwards, fresh gas from the bottle 650 may be filled into the reservoir 201 via valve 651, pipeline 617, valve 629 and finally valve 628.

Similarly, after a storage cell has been connected to the flange 503, the air within pipeline 504 can be pumped out via the tubing system 611, with valve 422 closed and valve 622 opened.

Prior to the beginning of operation of the apparatus, the optical pumping volume must be prepared specifically. To do so, the volume 320 is evacuated by the pump 601 via pipeline 208, purification unit 270, pipeline 207, valve 621, pipeline 610, valve 622 and tubing system 611. In order to efficiently cleanse the volume 320, this volume is baked out at a temperature in excess of 200° C. at the same time.

Whilst volumes 617 and 504 are built as small as possible (ca. 70 and 1 cm$^3$), the tubing system 611 is provided with a large cross section. At a conductance of 3.2 l/s (pipeline of length 2.2 m and diameter d=3.9 cm), 0.72 l/s and 0.2 l/s, respectively, a pump intake pressure of <3*10$^{-8}$ mb and an exhausting power of the pump of 68 l/s (for nitrogen), a pressure below 1*10$^{-5}$, 1*10$^{-5}$, 3*10$^{-6}$ mb is reached within the volumes 617, 504 and 320.

In order to minimize their length, the tubing systems described above are situated within the homogenous magnetic field (FIG. 3 100) as well. The magnetic field must not be distorted, in order to achieve, within the required volume, a homogeneity necessary for the storage of polarization, with relative, transversal gradients of, e.g.

$$\delta B_r/\delta r/B_0 = G_r < 5*10^{-4}/\text{cm}. \quad (20)$$

In order to obtain gradients below this value within a cylindrical volume of length 2.8 m and diameter 48 cm, an preferred system of 7 magnetic field coils, with equal diameter of 160 cm, was constructed. The three outer coils on either side are arranged in an axially symmetric manner relative to the central coil. In order to avoid relative field drifts, the coils are in serial electric connection. The necessary individual Ampere turns ratio was adjusted according to the number of wire turns.

All vacuum tubings are situated within the magnetic field 100. In order to preserve the field homogeneity, they are manufactured from iron-free materials. Generally, aluminum tubings are utilized, except for the polarization-conducting tubings 208, 323, 401 and 431. Knife-edge rings made of aluminum are used as gaskets. Aluminum knife-edge rings have the advantage, compared to normal gaskets made of polymers (synthetics, rubber like Viton, NBR etc.), that they do not gas out any more than the raw material itself, therefore a vacuum below 10$^{-6}$ mb is easily reached. Within the low pressure region 320, glass-metal interfaces are also sealed on a metal basis, using soft Indium. At the high pressure side (exit valve 420 and valve 422), Viton gasket rings are used. Of all polymers, Viton is most suitable due to its dense matrix and, consequently, its relatively low outgassing rates with respect to impurity gases like, e.g., $N_2$, $O_2$, $CO_2$, or hydrocarbons.

Within a system manufactured and sealed in this manner, a vacuum of $<5*10^{-9}$ mb is achieved next to the pumping lead. Compared to state-of-the-art techniques, where all the vacuum systems were made of glass, and only glass stop cocks with small cross-sections (maximum diameter 5 mm) and, consequently, low conductance could be employed, this is a crucial advantage.

FIG. 7 also shows the extension of the "fractional pumping" principle to the $^3$He-plasma volume. Advantageously, fractional pumping steps are realized here, too. After the volume 320 has been baked under vacuum conditions, and remaining impurities have been removed off the walls by means of a gas discharge and repeated exchange of the cleansing Helium gas, Helium-3 gas is introduced from the reservoir 201 via pipelines 202, 212, 203 and valves 210 and 213 into the purification unit 250. After an appropriate dwelling time, valve 214 is opened, and the gas flows into volume 320 via pipeline 206, 207, another gas purification unit 270 and pipeline 208. Another gas purification unit 402, identical to 270, is preferably situated at the exit of volume 320.

The gas purification units 270 and 402 serve to retain impurities (residual gases) which enter e.g. from valve 213 or valve 420; hence, the $^3$He gas is additionally cleansed. While valve 214 is manufactured in an ultra high vacuum compatible manner and, consequently, releases virtually no impurities, the valve 420 contains Viton gasket rings and the compressor contains a lubricant, which give off impurity gases. Furthermore, via the short connecting tubes 208 and 401 (conductance 4.3 l/s and 7.6 l/s, respectively), the gas purification units 270 and 402 serve as getter pumps to volume 320, as they can absorb gaseous impurities released within volume 320.

The gas purification units 270 and 402 contain both a titanium sublimation getter and a liquid nitrogen cold trap.

In order to separate the fractional pumping and the preparation of the apparatus with respect to the vacuum tubings, different pumps 601, 602 and 603 are preferably utilized for the evacuation tasks described before. Thus, inter-diffusion of impurity gases or vapors between the respective vacuum areas of the apparatus is prevented, and a maximum gas purity is accomplished within the volumes designed for optical polarization and storage of $^3$He. One has to distinguish between volumes that contain $^3$He during normal operation of the system, rear volumes of valves, and volumes in vicinity of the compressor drive which are exposed to oil vapors. A fourth sector, the intermediate volume 414 of the compressor, is preferably evacuated together with the rear volumes of the valves by a single pump 602. In addition, this configuration permits a constant evacuation of the rear and intermediate volumes of the valves and the compressor, independent of the need of evacuation of the relevant $^3$He working volumes. Furthermore, the tubing system for the evacuation of the $^3$He working volume is never contaminated with impurity gases from the rear and intermediate volumes of the valves and the compressor. This increases the reliability with which the required purity of $^3$He is reached, and sustained in the long run, within the $^3$He working volume. This is a prerequisite for a long, failure-free period of operation and, hence, for high mean production rates.

FIGS. 8*a,b* shows an inlet or evacuation valve of the compressor, with optimized cross-section, according to the invention. With the design of a compressor for the compression of nuclear spin polarized $^3$He gas, both the low pressure qualities and the high pressure qualities have to be considered. Low pressure qualities refer to good evacuation conditions, i.e. large valve cross sections towards the pump 601 and towards the optical pumping volume 320. High pressure qualities comprise, amongst others, small dead-space volumes within the valves 421 connecting to the intermediate storage cell, and within the valve 422 connecting to the storage cell. Furthermore, the dead volume in between the valves in the compressor head, and within the actual compression space 415, has to be minimized.

The exemplary realization meets these requirements. Valves 420 and 623 are designed as depicted in FIGS. 8*a,b*. A tappet rod 1020, rotationally-symmetrical to the symmetry axis 1040, opens into the compression space 415. Thus, gas can flow through the pipeline 1011 and the large outlet 1012, i.e. via a large cross-section, into the compression space, or the compression space can be evacuated efficiently. At closed position, the head of the tappet completely fills the outlet 1012, its surface terminating at level with the interior of the compression space (FIG. 8*a*). Thus, a large cross section 1012 and a small dead volume are combined successfully.

The remaining valves are constructed according to FIG. 4. Small cross sections of the drill-holes 1011, 1012 result in small dead volumes both towards the compression volume and towards pipelines 431 and 504. In addition, the tappet rod 1020 almost completely fills the valve volume, which contributes to the minimization of dead volumes.

In the exemplary realization, the cross sections of valves 420 and 623 are 300 mm$^2$. The cross sections of valves 421 and 422 are 20 mm$^2$ and 7 mm$^2$, respectively.

FIGS. 9*a* to 9*d* depict the valve 421, which is preferably built in an automatically opening manner. The drive 1030 can therefore take 3 positions. The drive 1030 moves the tappet to a definite closed position (FIG. 9*a*). Thereby, the tappet 1020 pushes an adjunct tappet 1024 against the outlet 1012. When the tappet 1020 is in the middle (FIGS. 9*c* and 9*d*), the adjunct tappet 1024 may be either in closed position (FIG. 9*c*) or in open position (FIG. 9*d*). FIG. 9*b* finally shows the tappet 1020 at the definite open position.

Figure 10:
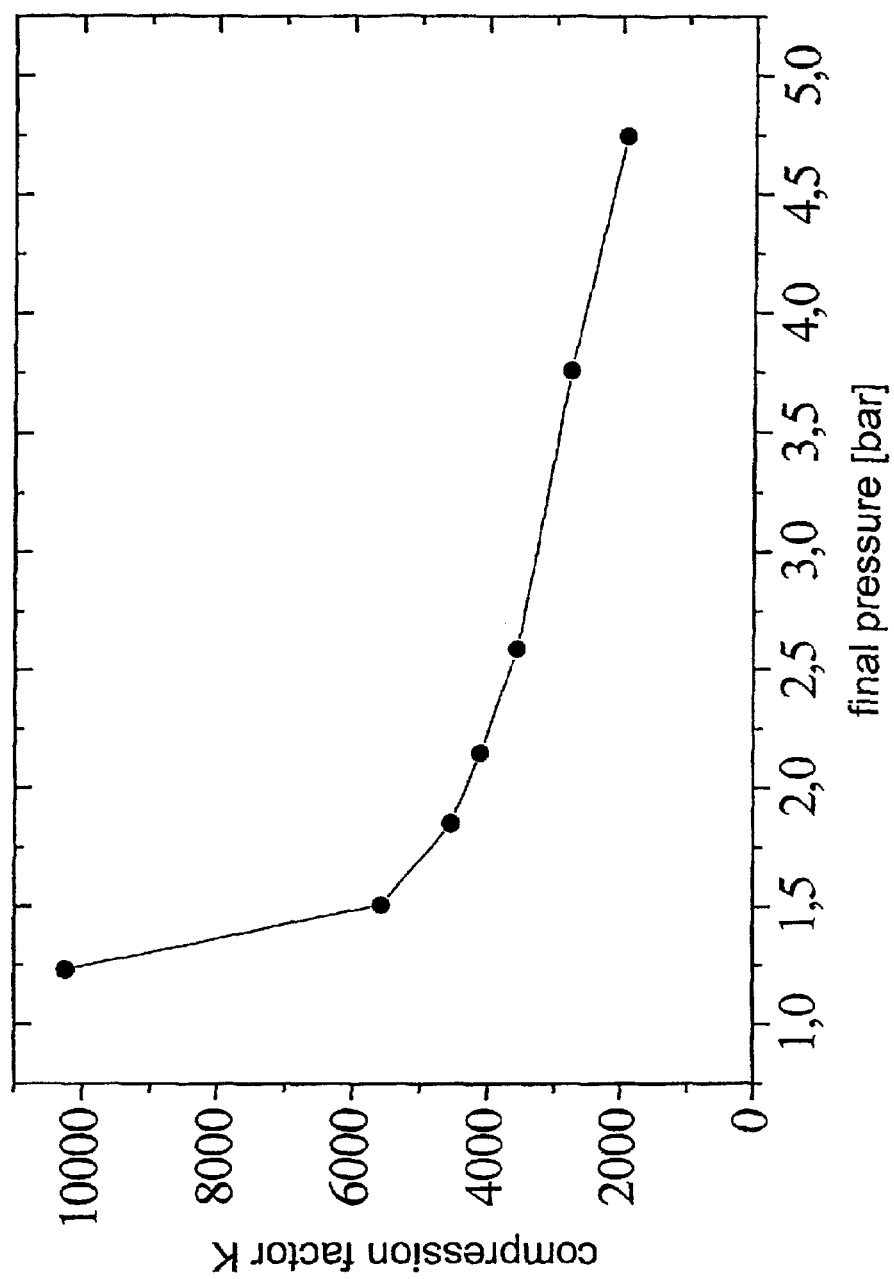

FIG. 10 depicts exemplarily the maximum achievable compression $K_0 = V_{stroke}/V_{dead}$ (see. eqn. (7)) in dependence on the final pressure $p_{501}$, i.e. the pressure within the storage cell 501. With respect to $K_0$, pressures $p_{501}$ within the storage cell 501 and $p_{440}$ within the intermediate storage cell 440 are equivalent. The decline from $K_0=10000$ at $p_{501}=1.5$ bar to $K_0=2000$ at $p_{501}=5$ bar is due to an elastic retreat of the gasket ring within notch 412, hence $V_{dead}$ increases according to eqn. (12) proportional to $\alpha \propto p_{501}$. This explains, according to eqn. (7), the hyperbolic decline of $K_0$ in FIG. 10. It can be seen from the diagram, that during the first compression into the intermediate storage cell 440, which involves a densification from $\approx 1$ mbar to 200 mbar, a value of $K_{eff}=200$ (corresponding to eqn. (6)) is normally not exceeded and, therefore, $K_0 > 10000$ holds.

Thus, a polarization transfer factor of at least $\eta_1 = 1 - 200/10000 = 98\%$ (eqn. (9) and (11)) is achieved (i.e. under the assumption of complete relaxation within $V_{dead}$). Indeed, within the accuracy of measurement of ±2%, no polarization losses during transfer were observed with the exemplary realization. For the subsequent compression into the storage cell 501, which involves densification from 200 mbar to 3 bar, FIG. 10 gives a value of $K_0=3000$. Taking into account the expansion of the gas from the intermediate storage cell 440 with volume $V_{440}=3.5$ l into the cylinder capacity with volume $V_{stroke}=15.4$ l, one obtains $$K_{eff2}=3 \text{ bar}/(0.2 \text{ bar}^*V_{440}/(V_{440}+V_{stroke}))\approx 80.$$

Assuming again complete relaxation within $V_{dead}$, one calculates for $\epsilon_2=K_{eff2}/K_0$ a value of 2%, and for the parameter $\eta_2$ (eqn. (11)) a value of $1-\epsilon_2=97.3\%$. Indeed, within the accuracy of measurement of ±2%, no polarization losses during transfer were observed within the second compression stage, either. Due to the large value of $K_0$, the total polarization loss during compression is limited to $1-\eta_1{}^*\eta_2=4.7\%$ at most. If one considers that the gas trapped in $V_{dead}$ obviously relaxes only partially, the total polarization loss is even lower. With the predecessor version, however, values were K=800 and $K_{eff}=200$, giving $\eta_1 \leq 0.75$. Thus the exemplary realization compresses polarized $^3$He much more efficiently.

On the other hand, FIG. 10 illuminates the necessity of a successive compression via an preferably introduced intermediate storage cell 440 serving as temporary storage. If, for instance, the gas was densified in one step from 1 mbar to 2 bar, about 50% of the compressed gas would remain within the dead volume, and one might have to take polarization transfer losses of up to 50%.

However, employing a two-stage compression from an initial pressure of 1 mbar, a final pressure of up to 10 bar can be envisaged, without having to worry about major polarization transfer losses. A compression to pressures greater than 10 bar is not sensible: According to the publication N. R. Newbury, A. S. Barton, G. D. Cates, W. Happer, H. Middleton; "Gaseous $^3$He—$^3$He magnetic dipolar spin relaxation"; Phys. Rev. A 48:6 (1993) 4411–4420, a mutual, so-called dipolar relaxation of the $^3$He atoms becomes relevant at high pressures, the rate of which is, at constant temperature T=273 K, proportional to the pressure, $$\Gamma_{1,dip(23^\circ\ C.)}=(p/\text{bar})/(744\ h). \quad (21)$$

At 10 bar pressure, this reduces the relaxation time to 75 h, independent of other, additional relaxation sources.

Advantageously, the method presented here and the exemplary realization make use of an intermediate storage cell 440 which displays a sufficiently long relaxation time. In the exemplary realization, a 3.5 l bulb made of Duran glass with $T_1 \approx 19$ h is utilized. Given a typical accumulation time of about 20 min, this gives rise to an additional polarization loss of 2.4%. Adding to this the losses in dead volumes discussed above, one obtains a total polarization transfer factor of at least $\eta=93\%$. If one considers that the gas trapped in dead volumes apparently relaxes only partially, this value is even higher.

It should be noted that in the exemplary realization, the polarization loss during the dwelling time of the gas within the total cylinder capacity of the compressor is negligible. A relaxation time of $T_1=13$ h was measured, which, according to eqn. (4), yields a very small surface specific relaxation coefficient of $\gamma=0.26$ cm/h. This compares favorably to the value of 4 cm/h in a compression stage according to state-of-the-art techniques, as described in J. Becker, W. Heil, B. Krug, M. Leduc, M. Meyerhoff, P. J. Nacher, E. W. Otten, Th. Prokscha, L. D. Schearer, R. Surkau; "Study of mechanical compression of spin-polarized 3He gas." Nucl. Instrum. Methods A 346 (1994) 45–51.

Advantageously, in the apparatus described in the invention, the final processing of the interior of the compression space was carried out using non-magnetic tools only. Common turning steels leave burn traces in titanium, which, after ultrasonic cleansing, become visible as stains of iron oxide. Should the iron not be completely oxidized, ferro-magnetic areas are introduced into the surface, which then cause a strong relaxation. Furthermore, the compression space was lubricated with a resistant grease which has a very low outgassing rate and good relaxation properties.

According to the invention, the application of a single piston pump, which serves both intermediate storage and final storage, preferably reduces expenditures with respect to original costs and maintenance charges. Viewed statistically, the decreased failure probability due to a reduced number of mechanical parts warrants a higher reliability and, therefore, a prolonged operating time. Ultimately, this benefits an increased production rate between the service intervals required for the maintenance of the apparatus.

FIGS. 11a and 11b depict a fast moving variant of the principle of an extrapure gas compressor presented here, with smaller stroke volume and reduced stroke length but equal production capacity. The principle of fractional pumping via intermediate volumes, e.g. as shown in FIG. 5a, is retained. The gear drive of the piston 415 can be preferably realized in a traditional manner via crankshaft 481a,b and conrod 480a,b. Two versions with outer (FIG. 11a) and inner (FIG. 11b) gear drive are shown.

The noble gas quantity leaking from the working volume via gasket ring 412, 413 into the intermediate vacuum region 418 is pumped out via valve 627 by the high vacuum pump 603, and is stored in a reservoir 221. After the separation of impurity gases, e.g. using cryogenic technology as described in DE 199 27 773.7, the purified noble gas is available once again. Since a fast moving piston gives rise to increased leakage rates of the gasket rings, another intermediate chamber 414 is added in front of the intermediate volume 418 and evacuated via the pumping lead 626.

Figure 12:
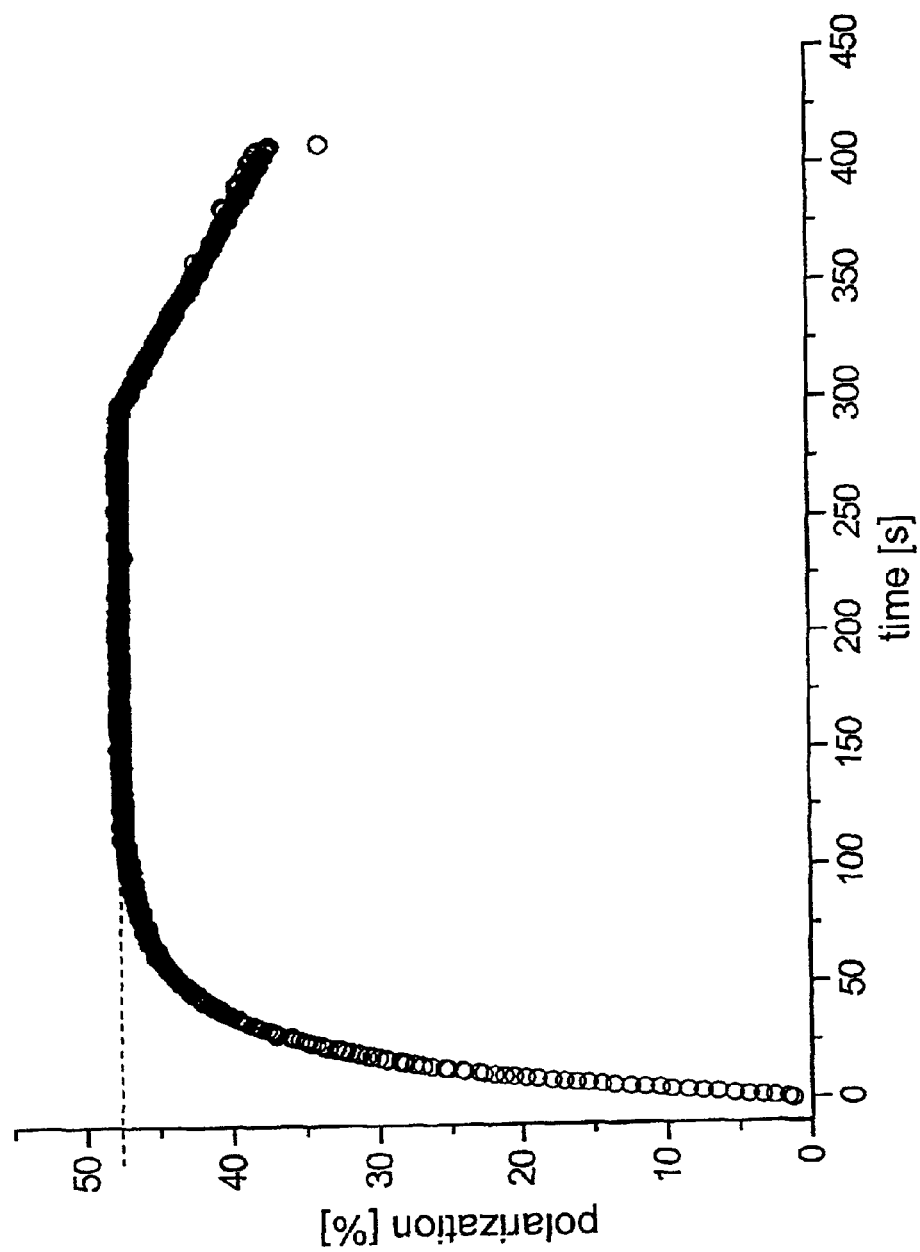

FIG. 12 shows the temporal evolution of the polarization in one of the cells of volume 320. The cell is first filled with unpolarized gas, then the resonant, circularly polarized 1083 nm laser light is coupled in. In order to obtain long absorption lengths and to absorb as much laser light as possible, the volume was allocated to 5 cells, of 2.4 m length each, in the exemplary realization. The resonant laser power was approximately 5 Watt. At typical pressures, the polarization build-up within the long 5.5 liter gas volume takes about 1 minute, after which a value of 93% of the steady state polarization is reached. The rise in polarization, very steep at first, gradually flattens with increasing polarization levels and finally approaches a steady state value (dashed line), which is below 100% due to competing relaxation processes discussed above.

Figure 13:
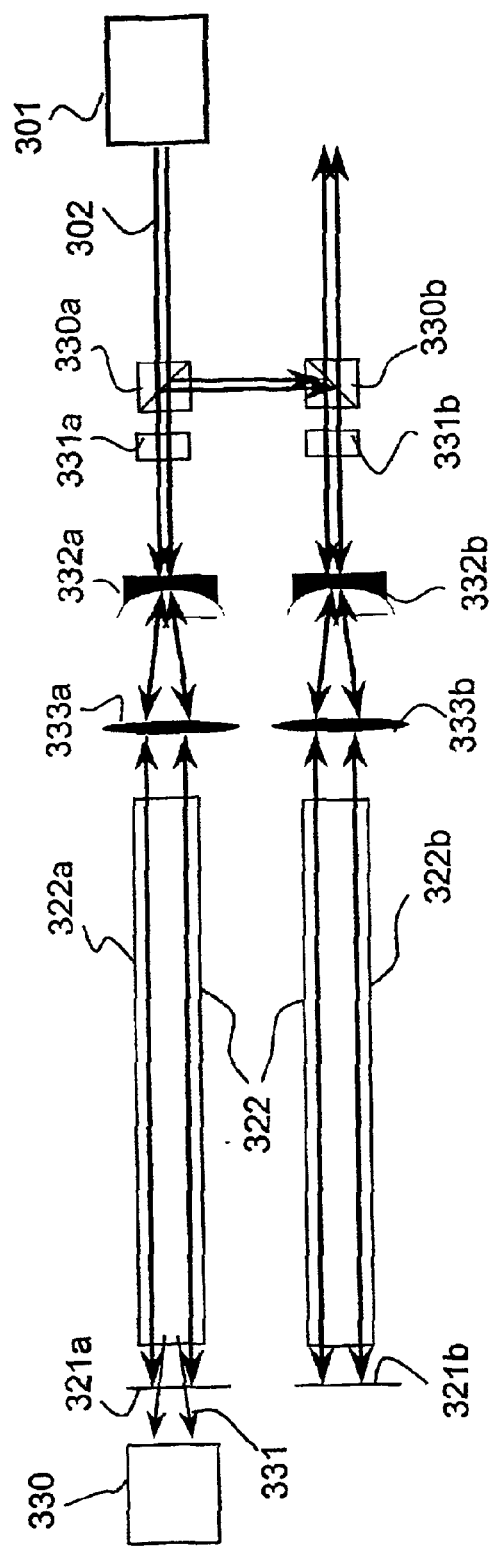

FIG. 13 shows how the laser light beam 302 is broadened and made parallel. The light must be completely circularly polarized prior to its entry into the optical pumping volumes, e.g. 322a, 322b. Advantageously, the laser beam is first linearly polarized by a high quality polarizing cube beam-splitter 330a and then circularly polarized by an appropriately adjusted quarter-wavelength retardation plate 331a. Subsequently, a telescope 332a, 333a widens the beam to the desired diameter and projects the image of the intermediate focus onto the opposite mirror 321a, filling as much of the cell volume as possible, i.e. the beam is weakly convergent. Given the long pathways through cells 322a, 322b, which are 2*240 cm in the exemplary realization, it is preferred to re-collimate the beam, after back and forth reflection through a cell, by lenses 333a, 332a, before it is guided into another cell. By means of this sequence of beam forming lenses 333a, 332a, the light does not come into contact with the cell walls 322a or 322b, in spite of a beam diameter well adapted to the cell diameter. The beam waist, of largest possible width, is preferably situated at the location of the rear mirror 321a or 321b. Otherwise, reflection of light at the cell tubing would decrease the degree of circular polarization and lead to additional relaxation. The telescope preferably consists of a concave lens 332a and a convex lens 333a. This shortens the length of the telescope and limits the divergence to relatively small angles. The latter has to be considered in order to maintain the circular polarization, despite an anti-reflective coating of the lenses.

Advantageously, the laser beam 302 is guided successively, in a sense from higher to lower $^3$He-polarization, through all the cells (322a and 322b in the example) of a compartment 322, in order to efficiently exploit the available absorption length, as explained above. Thus, as much light as possible is used; in particular, the highest possible polarization rate is attained within the compartment with maximum polarization and, hence, the lowest absorption probability. After a second passage through the telescope 332a, 333a and back through the polarizing optics 331a, 330a, the beam is finally linearly polarized once more, with small diameter. Since the linear polarization is rotated by 90°, the beam is reflected out of the beam splitter cube perpendicular to its incident direction. An equal optical configuration, consisting of a polarizing cube beamsplitter 330b, a quarter-wavelength retardation plate 331b and a telescope 332b, 333b, deflects the beam towards the next cell 323, restores the circular polarization and broadens the beam again.

Figure 14A:
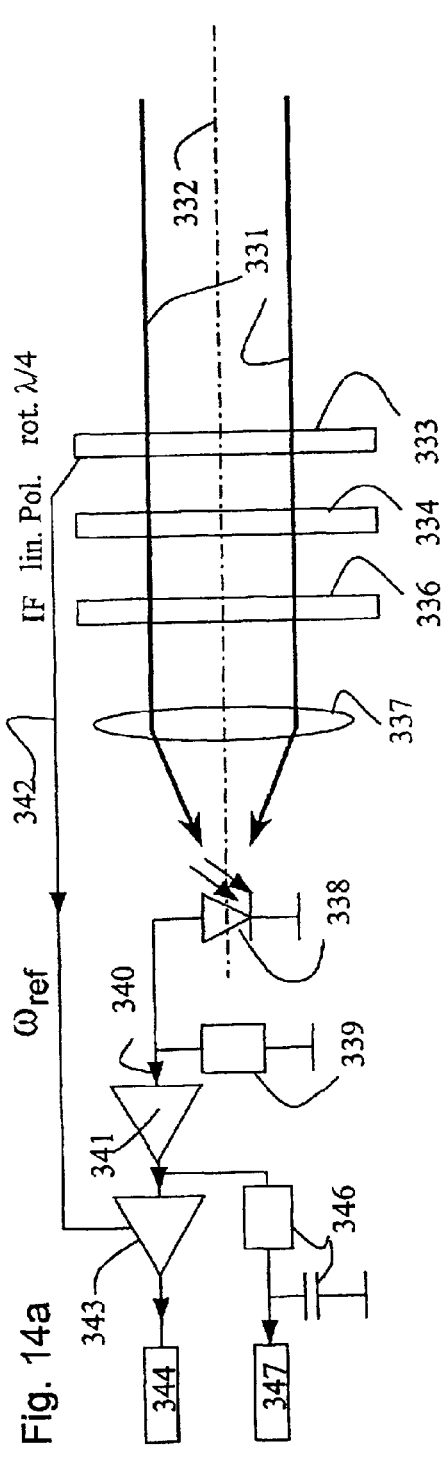

FIGS. 14a,b shows a measurement setup to determine the level of nuclear polarization of $^3$He within the optical pumping cells. The mirror 321a is manufactured in a dichroitic manner, highly reflective for 1083 mm, highly transmissive for 668 nm. On the one hand, it reflects back the pumping light behind the cell 322a, on the other hand, it transmits fluorescence light that is emitted out of the optical pumping cells along the optical axis 332. Its degree of circular polarization is used to compute, via gauge factors, the nuclear polarization of $^3$He.

To do so, the degree of circular polarization of the escaping fluorescence light is converted, via a quarter-wavelength retardation plate 333 rotating at frequency f, into linearly polarized light, the polarization axis of which rotates at frequency f as well. After passing through a static linear polarizer 334, an interference filter 336 and a collimator 337, the light is transformed by a photo detector 338, e.g. a photo diode, into a current signal which is amplitude-modulated with frequency 2f. After amplification by the amplifier 341, the periodic modulation is further amplified by a lock-in amplifier 343, rectified phase-sensitively and recorded on memory 344. The contribution of unpolarized light results in a non-zero mean value signal, which is measured by means of a low-pass filter and recorded on memory 347. The ratio of the values in memory 344 and 347 is the searched-for level of circular polarization. Divided by a known, pressure-dependent gauge factor, it yields the absolute value of the nuclear polarization.

Figure 14B:
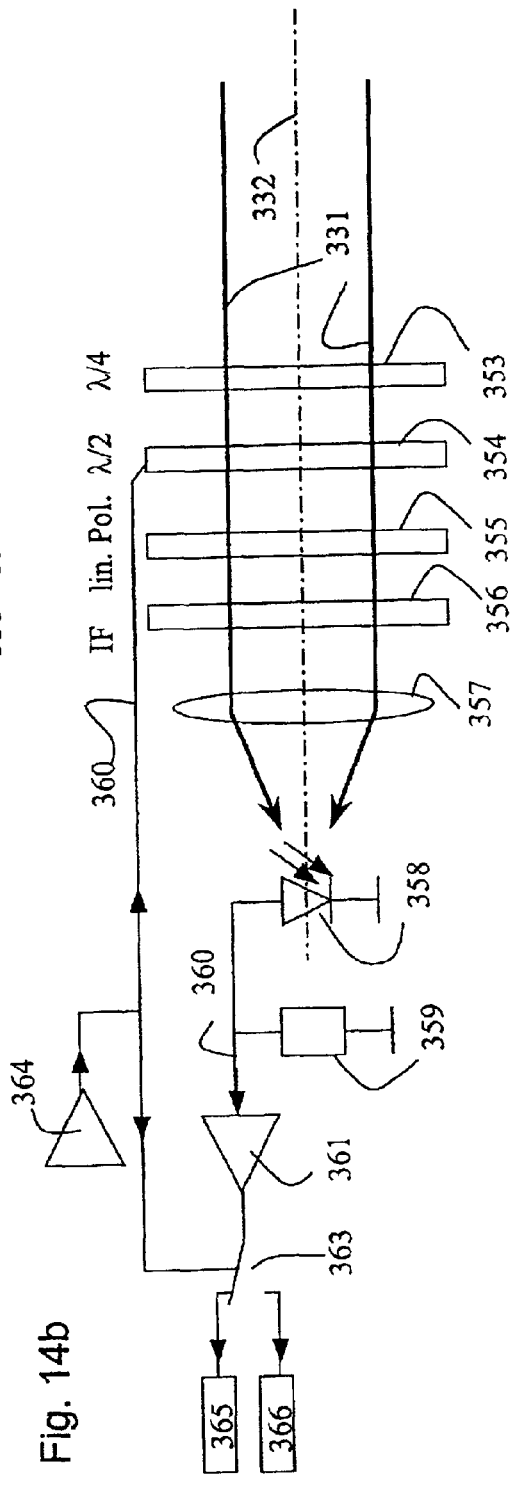

FIG. 14b describes a new variant of the method, which employs a preferred detection system without any rotating mechanical elements. This configuration generates, in dependence on the fluorescence circular polarization, a maximum and a minimum voltage value, the difference of which, divided by the sum and the pressure-dependent gauge factor, yields once again the nuclear polarization. In this setup, the 668 nm light first passes a static quarter-wavelength retardation plate 353, then a liquid crystal element 354, a linear polarizer 355, a 668 nm interference filter 356 and a collimator 357, before it is detected in a photo detector 358 and amplified by an amplifier 361. A square wave signal generator 364 produces a positive or negative voltage signal on line 360, which, upon application of one of the two voltage values but not the other, makes the liquid crystal element 354 act as a half-wave plate. Hence, the plane of polarization is rotated periodically by 90°. The analyzer 355 thus transmits alternately the fraction of the fluorescence light with left handed or right handed polarization; the corresponding current signal is, depending on the control voltage signal on line 360, recorded on memory 365 and 366, respectively, by means of a switch driven by the same control voltage signal. From these two values the nuclear polarization can be computed, as stated above.

Figure 15:
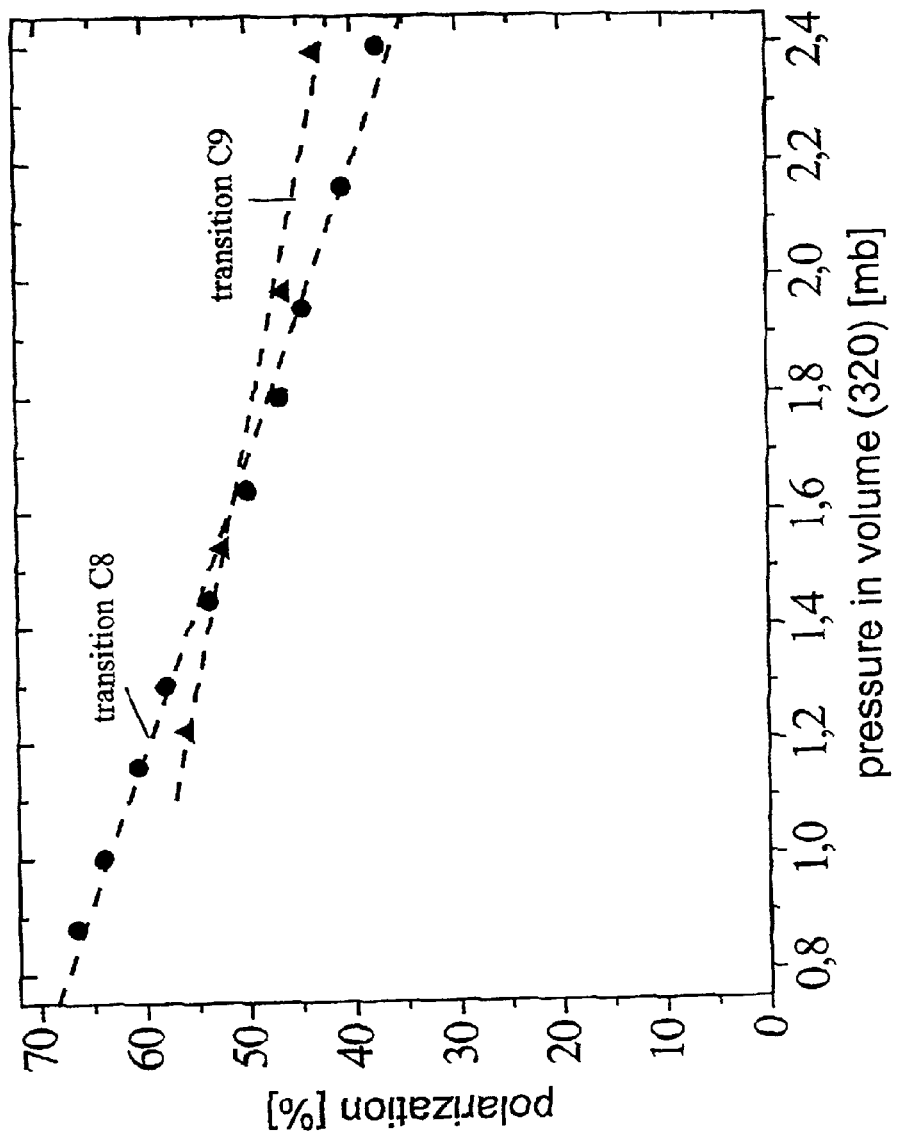

FIG. 15 shows the steady state polarization attainable in an exemplary optical pumping configuration, e.g. as depicted by the dashed line, in dependence on the gas pressure. At minimum pressure a maximum steady state polarization is reached. Its value drops with a gradual increase in pressure. Furthermore, the different efficiency of the two optical transitions C8 and C9 of the $^3$He* atom is shown. At lower pressures, transition C8 leads to a higher final polarization.

Figure 16:
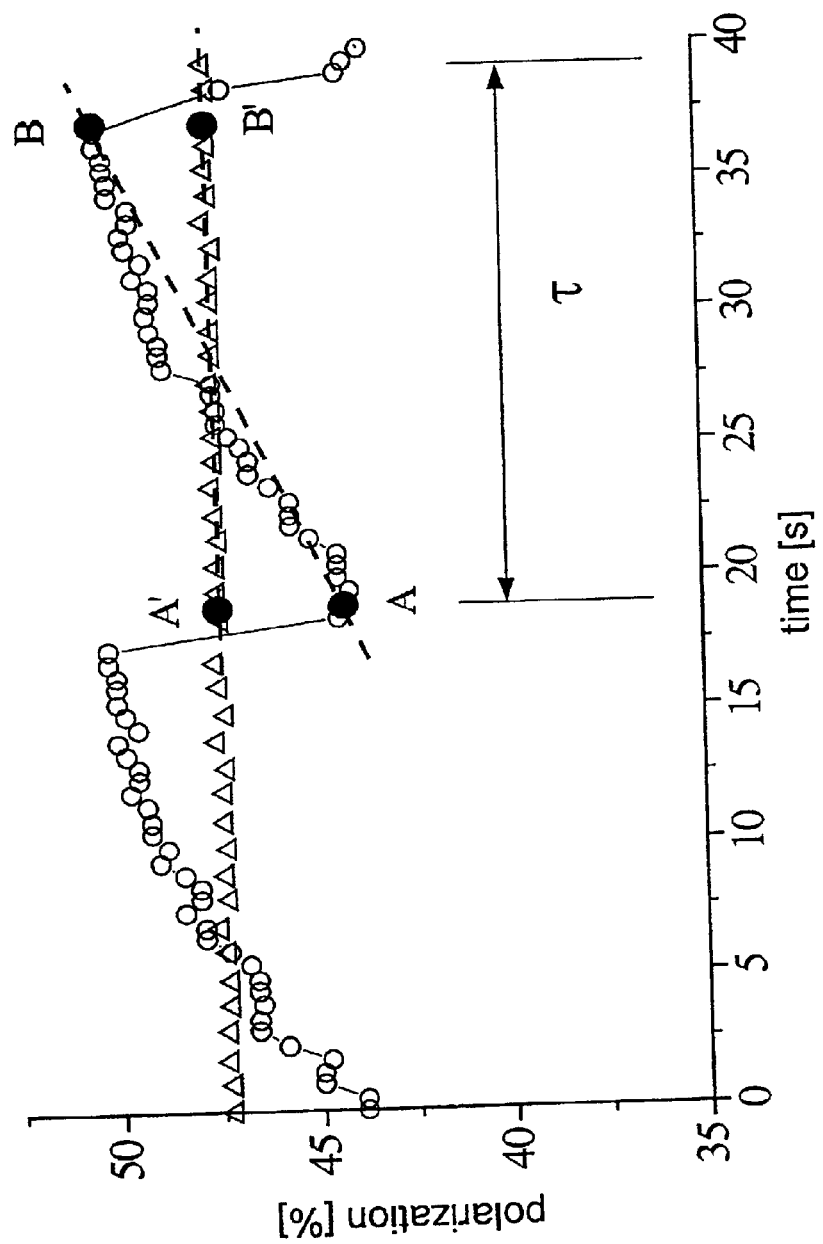

FIG. 16 shows exemplarily, that the configuration for optical pumping of $^3$He described in the invention, according to FIGS. 3 and 13, yields higher polarization rates if the gas supply employed is discontinuous rather than continuous. In the second case, gas of a lower polarization degree flows continuously into the optical pumping cells. In the configuration illustrated in FIG. 3, however, both the gas supply for the optical pumping volume 320 and the transport of gas into the compressor 410 take place in a discontinuous way. To do so, the quantity of gas introduced from reservoir 201 via pipelines 202, 212 and valves 210, 213 into the purification unit 250 exactly matches the amount of gas that flows, at a given pressure, out of the optical pumping volume 320 and into the evacuated compression space 415, once valves 214 and 420 are opened. The exchange of gas happens quasi instantaneously, so that within each cell 323, new, lower polarization values come about immediately. Consequently, as shown in FIG. 16, the polarization build-up after the exchange of gas advantageously starts with the high polarization rate that is typical for the considerably lower polarization prevailing now (comp. the steep rise in polarization at point A in FIG. 16). Additionally, the polarization build-up becomes generally steeper due to the omission of the current induced relaxation rate $\Gamma_{1,curr}$. Hence the increase in polarization of the gas during one cycle period is, on the whole, larger in the case of this "fractional optical pumping" than upon a continuous supply of gas. Starting at point A, a higher final polarization B is reached, whereas in the case of a continuous supply of gas, the polarization develops from A' to B'.

Thus, the discontinuous exchange of gas in volume 320 described above leads to a preferred higher final polarization. To accomplish a pre-set production rate, the compressor must be filled with a certain gas quantity, corresponding to the pressure $p_{in}$ determined by the cylinder capacity. In the realization according to state-of-the-art techniques, described in Surkau 1995 and Surkau et al. 1997, this pressure ensues from the expansion of the gas out of the optical pumping volume. The pressure during polarization is therefore greater than the pressure at the start of the compression. As can be seen from FIG. 15, one then has to take a loss with respect to the final polarization. With the new technique described here, the pressure within the optical pumping cells 323 remains stable, after a rather short interval during which gas flows into the compressor and is replenished immediately by gas from the purification unit, at the value $p_{in}$, and does not exceed this value during the polarization phase. Thus, a higher final polarization is attained at an equal production rate.

Figure 17:
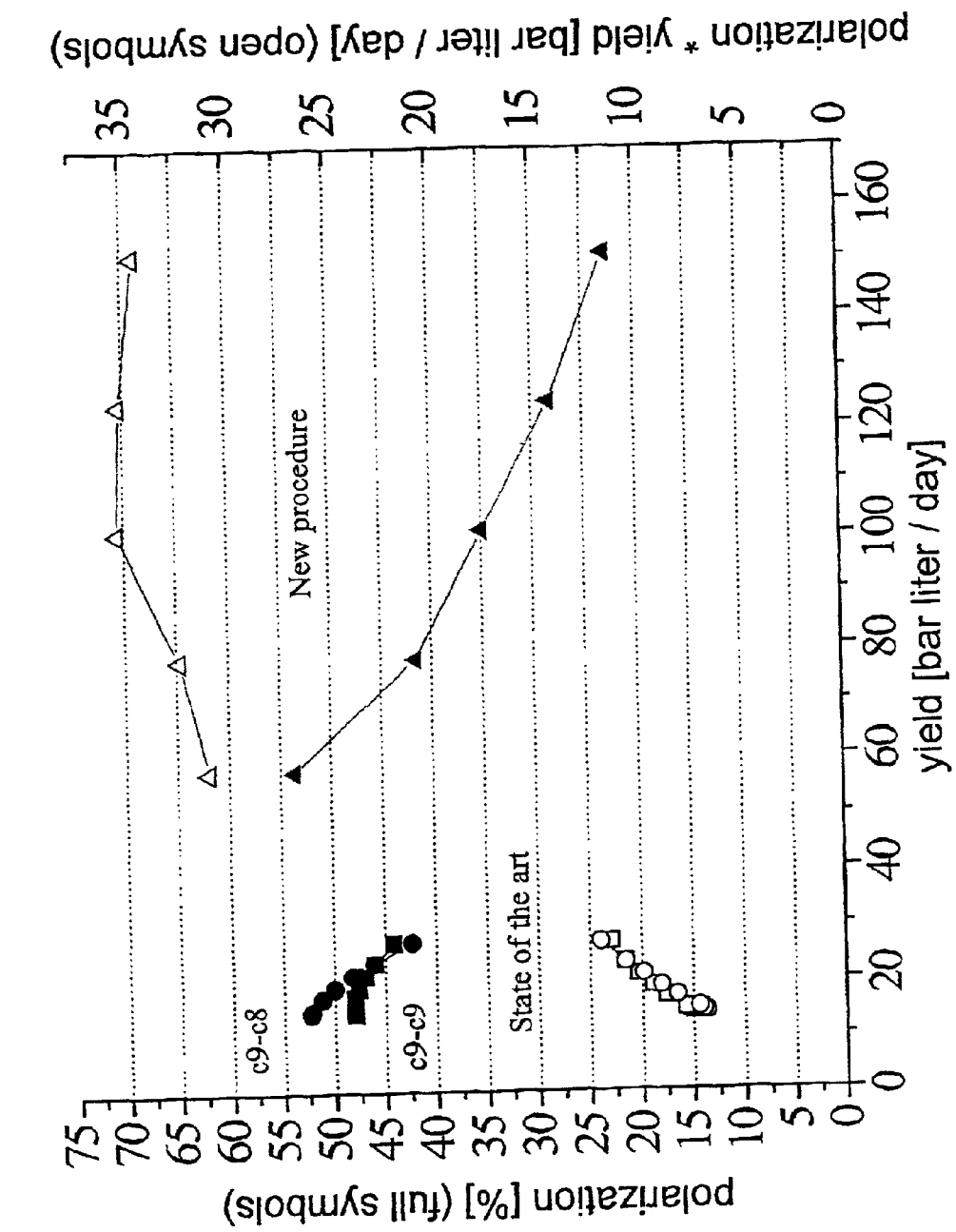

FIG. 17 compares the production capacity of the system according to state-of-the-art techniques and of the system described in the invention, the latter being operated preliminarily without active purification units 270 and 402. With a compression cycle time of 20 s and upon application of 8 W of resonant laser light tuned to the optical transition C9 of $^3$He*, $^3$He is polarized to more than 50% with a production rate of 60 bar liters/day. With increasing production rates, the attainable polarization drops, according to FIG. 17. The product of rate and final polarization, however, even increases slightly; this is a measure of the total number of polarized atoms dissolved in non-polarized $^3$He. Therefore, if the application requires a maximum number of polarized $^3$He atoms diluted in an arbitrary quantity of buffer gas, then the shown production rates at high pressure are preferred.

If these production rates are compared with those of state-of-the-art techniques, the preliminary mode of operation already yields a flux increased by a factor of five (FIG. 17) with an equal final polarization of more than 50%. With respect to highest production rates, the flux was increased by more than one order of magnitude, and the production rate, expressed in % bar liters/day, by a factor of 5. Furthermore, upon application of the purification units 270 and 402, a preferred increase of the final polarization to values greater than 60% can be reached.

What is claimed is:

1. A device for the production of nuclear spin polarized fluids comprising:
   an assembly for optical pumping a medium in a low pressure plasma to produce a polarized medium;
   a compressor assembly connected to the optical pumping assembly for compressing the polarized medium; and
   a storage volume connected to the compressor assembly for storing the polarized medium, wherein the compressor assembly comprises at least one ultra high vacuum (UHV) compatible lead through, including:
   a housing;
   a first space within the housing and connected via a first port to a space outside the UHV-compatible lead through;
   a second space within the housing and connected via a second port to the optical pumping assembly;
   a movable component separating the first space from the second space via an intermediate space; and
   a seal for limiting a penetration of volatile media from the first space into the second space.

2. A device according to claim 1, further comprising a plurality of first valves for coupling the assembly, the compressor, and the storage volume, wherein individual ones of the plurality of first valves include an ultra high vacuum (UHV) compatible lead through.

3. A device according to claim 2, wherein individual ones of the plurality of first valves are gathered into valve blocks.

4. A device according to claim 3, wherein the valve blocks further comprise intermediate vacua common for a number of first valves, and wherein the intermediate vacua are connected to each other via bores.

5. A device according to claim 4, wherein at least one of the valve blocks comprise at least one of an inlet valve from the optical pumping assembly to the compressor assembly or an outlet valve from the compressor assembly into the storage volume.

6. A device according to claim 4, wherein at least one of the valve blocks comprise at least one second valve for at least one of evacuating the optical pumping assembly, controlling flows of the polarized medium, or controlling pressure monitors.

7. A device according to claim 2, further comprising a pipeline system for transport of the polarized medium and evacuation connected to the assembly, the compressor, and the storage volume, including outgassing aluminum tubes, fastened by rings.

8. A device according to claim 2, further comprising a getter that is selectively absorbing positioned in a flow ahead or after the optical pumping assembly.

9. A device according to claim 8, wherein the getter is two or more getters that comprise nonferromagnetic getter substances.

10. A device according to claim 8, wherein the getters are evaporation getters.

11. A device according to claim 9, wherein the nonferromagnetic getter substances comprise little relaxing titanium.

12. A device according to claim 9, wherein the nonferromagnetic getter substances comprise bismuth.

13. A device according to claim 10, wherein the optical pumping assembly comprises at least one evaporation getter.

14. A device according to claim 13, wherein the at least one evaporation getter is part of the optical pumping assembly and is operated as a cathode in a plasma region of the optical pumping assembly in order to selectively bind gases other than the polarized medium.

15. A device according to claim 10, wherein the evaporation getters comprise cooling set-ups.

16. A device according to claim 7, further comprising:
   a cylinder head of the compressor having a dead volume;
   at least one of the plurality of first valves coupling the compressor assembly to the storage volume; and
   a portion of the pipeline system connected to the storage volume,
   wherein the dead volume is minimized in order to enable a fast and substantially complete polarized medium transport from the compressor assembly to the storage volume.

17. A device according to claim 16, wherein the compressor comprises a stroke volume such that a fraction of gas remaining and relaxing in the dead volume is minimized.

18. A device according to claim 2, wherein the compressor assembly comprises a compressor cylinder, and wherein the compressor cylinder has a ratio of a circumference to a stroke volume of the compressor assembly that is smaller than about $1/(30 \text{ cm}^2)$.

19. A device according to claim 2, wherein the optical pumping assembly comprises at least one long cell containing the optically pumped low pressure plasma.

20. A device according to claim 19, the at least one long cell comprises a plurality of mirrors that serve to double an absorption path length of pumping light within the at least one long cell, thereby conserving a degree of circular polarization.

21. A device according to claim 20, wherein the plurality of mirrors are transparent for certain spectral lines of $^3$He.

22. A device according to claim 2, wherein the optical pumping assembly has a light source that has a spectral distribution that is adapted to a Doppler-width of an absorption line of a noble gas.

23. A device according to claim 22, wherein the light source is a laser light source and for a given laser power the cross section of a laser beam emitted from said laser light source is formed such that a resulting light intensity will not surpass a saturation value of a maximum optical pumping rate.

24. A device according to claim 19, wherein the optical pumping assembly comprises imaging optical elements arranged outside the at least one long cell in order to focus a beam from a light source of the optical pumping assembly such that a cross section of the beam remains smaller than a cross section of the at least one long cell in order to prevent depolarizing reflection from walls of the at least one long cell.

25. A device according to claim 19, wherein the at least one long cell has at least an entrance window and an outlet window that include glass of optical quality.

26. A device according to claim 25, further comprising an element for determining a degree of circular polarization of light, wherein the degree of circular polarization is determined by taking a difference of a maximum and a minimum measured voltage value and dividing it by their sum, wherein the maximum and minimum voltage values are obtained by passing the light first through a $\lambda/4$ retardation plate followed by a liquid crystal element and finally a linear polarizer after which the light generates in a photo detector a first voltage value, and wherein the first voltage value is the maximum or the minimum measured voltage value depending on a positive or negative voltage signal applied to the liquid crystal element which reacts by forming a bi-refringent optical delay plate having delays of either an even or an odd multiple of half of a wave length $\lambda/2$ or vice versa.

27. A device according to claim 26, wherein the element for determining the degree of circular polarization determines a degree of nuclear polarization of a noble gas plasma.

28. A device according to claim 1, wherein the optical pumping assembly comprises at least one high frequency driven electrode powering the low pressure plasma.

29. A device according to claim 4, wherein the intermediate vacua are connected to the optical pumping assembly.

30. A device according to claim 29, further comprising a purification assembly for purifying a gas pumped out of the intermediate vacua, and wherein the purified gas is recycled within the device.

31. A procedure for producing nuclear spin polarized gasses comprising:

optically pumping a gas in a low pressure plasma to produce a polarized gas;

mechanically compressing the polarized gas using a fractional pumping method; and transporting the gas into a storage volume.

32. A procedure according to claim 31, wherein the fractional pumping method is performed by an ultra high vacuum (UHV) compatible lead through including:

a housing;

a first space within the housing and connected via a first port to a space outside the UHV-compatible lead through;

a second space within the housing and connected via a second port to a closed system containing the polarized gas;

a movable component separating the first space from the second space via an intermediate space; and a seal for limiting a penetration of volatile media from the first space into the second space.

33. A procedure according to claim 31, wherein the production of the nuclear spin polarized gases is performed using a device comprising:

an assembly for optical pumping gasses in a low pressure plasma to produce polarized gasses;

a compressor assembly for compressing the polarized gases; and a storage volume for storing the polarized gasses, wherein the compressor assembly comprises at least one ultra high vacuum (UHV) compatible lead through, including:

a housing;

a first space within the housing and connected via a first port to a space outside the UHV-compatible lead through;

a second space within the housing and connected via a second port to the device;

a movable component separating the first space from the second space via an intermediate space; and a seal for limiting a penetration of volatile media from the first space into the second space.

34. A procedure according to claim 32, further comprising actively pumping the intermediate space.

35. A procedure according to claim 31, wherein the gas is purified of contaminants by getter devices before and/or during at least one of the optical pumping or mechanically compressing.

36. A procedure according to claim 35, wherein the getter devices are cooled.

37. A procedure according to claim 36, wherein the getter devices are cooled to a temperature of liquid nitrogen.

38. A procedure according to claim 31, wherein the mechanically compressing is performed by a single compressor up to a pressure of less than 10 bar.

39. A procedure according to claim 31, wherein the fractional pumping method yields noble gas and the procedure includes:

purifying and recycling the noble gas; and producing polarized noble gas.

40. A device according to claim 2, wherein the compressor assembly comprises a compressor cylinder, and wherein the compressor cylinder has a ratio of a circumference to a stroke volume of the compressor assembly that is smaller than about $1/(100 \text{ cm}^2)$.

41. A device according to claim 2, wherein the compressor assembly comprises a compressor cylinder, and wherein the compressor cylinder has a ratio of a circumference to a stroke volume of the compressor assembly that is smaller than about $1/(300 \text{ cm}^2)$.

* * * * *